United States Patent
Rocchi et al.

(10) Patent No.: US 10,125,165 B2
(45) Date of Patent: Nov. 13, 2018

(54) SOLUTION PHASE SYNTHESIS AND CRYSTALLIZATION OF BETA-TURN PEPTIDOMIMETIC CYCLIC SALTS

(71) Applicant: Mimetogen Pharmaceuticals, Inc., Montreal, Quebec (CA)

(72) Inventors: Sébastien Rocchi, Hoenheim (FR); Chantal Devin, Lingolsheim (FR); Wei Tian, Södertälje (SE); Martin Bohlin, Johanneshov (SE)

(73) Assignee: MIMETOGEN PHARMACEUTICALS, INC., Montreal, Quebec (CA)

( * ) Notice: Subject to any disclaimer, the term of this patent is extended or adjusted under 35 U.S.C. 154(b) by 0 days.

(21) Appl. No.: 15/205,909

(22) Filed: Jul. 8, 2016

(65) Prior Publication Data
US 2017/0008923 A1 Jan. 12, 2017

Related U.S. Application Data

(60) Provisional application No. 62/190,596, filed on Jul. 9, 2015.

(51) Int. Cl.
| | |
|---|---|
| *A61K 38/12* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 5/113* | (2006.01) |
| *C07K 1/30* | (2006.01) |
| *C07K 1/02* | (2006.01) |
| *C07K 5/10* | (2006.01) |

(52) U.S. Cl.
CPC .............. *C07K 5/1021* (2013.01); *C07K 1/02* (2013.01); *C07K 1/306* (2013.01); *C07K 5/1027* (2013.01); *C07B 2200/13* (2013.01)

(58) Field of Classification Search
CPC ...... A61K 38/00; A61K 38/12; C07K 5/0215; C07K 1/306; C07K 7/50
See application file for complete search history.

(56) References Cited

U.S. PATENT DOCUMENTS

2012/0165271 A1* 6/2012 Cumberlidge ......... A61K 38/12
514/20.8

FOREIGN PATENT DOCUMENTS

WO 2013/191926 A1 12/2013

OTHER PUBLICATIONS

Norgren et al., [beta] 2-Amino Acids in the Design of Conformationally Homogeneous cyclo-Peptide Scaffolds, The Journal of Organic Chemistry, Sep. 1, 2006, pp. 6814-6821, vol. 71(18).
Chakraporty et al., Antitumor and Antimicrobial Activity of Some Cyclic Tetrapeptides and Tripeptides Derived from Marine Bacteria, Marine Drugs, May 15, 2015, pp. 3029-3045, vol. 13(5).
Feng et al., Solid-Phase Snar Macrocyclizations to Give Tunr-Extended-Turn Peptidomimetics, Chemistry—A European Journal, Wiley—VCH Verlag GMGH & Co. KGGA, Weinheim, DE, Jan. 1, 1999, pp. 3261-3272, vol. 5(11).
Maliartchouk et al., A Designed Peptidomimetic Agonistic Ligand of TRKA Nerve Growth Factor Receptors, Molecular Pharmacology, American Society for Pharmacology and Experimental Therapeutics, US, Feb. 1, 2000, pp. 385-391, vol. 57(2).
Feng et al., Snar Cyclizations to Form Cyclic Peptidomimetics of Beta-Turns, Journal of the American Chemical Society, American Chemical Society, US, Jan. 1, 1998, pp. 10768-10769, vol. 120(41).
Sewald et al., Peptides: Chemistry and Biology, 2002, p. 142, Wiley-VCH Verlag GmbH & Co. KGaA.
Greene et al., Protective Groups in Organic Synthesis, Second Edition, 1991, John Wiley and Sons, New York, NY, USA.

* cited by examiner

*Primary Examiner* — Rachael E Bredefeld
*Assistant Examiner* — Kaipeen E Yang
(74) *Attorney, Agent, or Firm* — Pillsbury Winthrop Shaw Pittmann LLP

(57) ABSTRACT

The present disclosure relates to methods of preparing and crystallizing β-turn cyclic peptidomimetic salts of formula I:

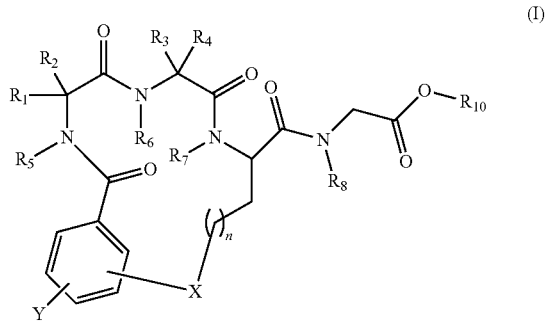

(I)

where $R_1$, $R_2$, $R_3$, $R_4$, $R_5$, $R_6$, $R_7$, $R_8$, $R_{10}$, X, Y and n are as defined in the specification.
The present disclosure provides a more efficient route for preparing a crystalline form of β-turn cyclic peptidomimetic compounds and salts thereof.

12 Claims, 24 Drawing Sheets

SOLUTION PHASE SYNTHESIS AND CRYSTALLIZATION OF BETA-TURN PEPTIDOMIMETIC CYCLIC SALTS

CROSS-REFERENCE

This application claims the benefit of priority to U.S. Provisional Patent Application No. 62/190,596, filed on Jul. 9, 2015, the entire contents of which are incorporated herein by reference.

FIELD OF THE INVENTION

The disclosure relates to methods of preparing crystalline forms of β-turn cyclic peptidomimetic salts.

INTRODUCTION

Considering the promising pharmacological activity of several compounds in the class of β-turn cyclic peptidomimetic compounds, there exists a need for the development of a new synthetic methodology that allows for scalability and/or cost effective production.

It is therefore an aspect of this invention to provide new synthetic methods for the preparation of β-turn cyclic peptidomimetic compounds. It is a further aspect of this invention to provide commercially viable methods to produce these compounds.

It would be advantageous to develop a method of crystallizing or precipitating β-turn cyclic peptidomimetic salts to provide an improved purification method for these salts. In addition, a crystalline or highly purified precipitated form of β-turn cyclic peptidomimetic salts would be useful in formulating pharmaceutical compositions. Thus, there is a need for methods to produce crystalline or precipitated β-turn cyclic peptidomimetic compounds or salts thereof.

SUMMARY OF THE INVENTION

In various embodiments, the invention provides synthetic methods for β-turn cyclic peptidomimetic salts. Synthetic methods are illustrated in the embodiments denoted in FIG. 1 (Scheme 1).

Certain embodiments of the present disclosure provide a method of preparing a crystalline salt of a β-turn peptidomimetic cyclic compound of formula (I)

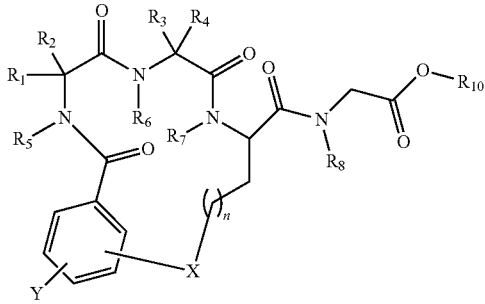

(I)

wherein:

$R_1$ is hydrogen, $C_1$ to $C_6$ alkyl, aryl, or a amino acid side chain substituent of a natural or unnatural amino acid;

$R_3$ is hydrogen, $C_1$ to $C_6$ alkyl, aryl, or a amino acid side chain substituent of a natural or unnatural amino $R_2$ and $R_4$ are independently hydrogen or $C_1$ to $C_6$ alkyl, or $R_1$ and $R_2$ together with the carbon atom to which they are attached form a cyclopropyl, cyclobutyl, cyclopentyl or cyclohexyl group, or $R_1$ and $R_2$, $R_3$ and $R_4$ together with the carbon atom to which they are attached form a cyclopropyl, cyclobutyl, cyclopentyl or cyclohexyl group;

Y is selected from the group consisting of hydrogen, $-NO_2$, $-COOR_{14}$, $-OC(R_{14})_3$, $-SO_3R_{14}$, and $-SO_2R_{14}$;

$R_5$, $R_6$, $R_7$ $R_8$, and $R_9$ are independently hydrogen or $C_1$ to $C_6$ alkyl;

$R_{10}$ is hydrogen, methyl, t-butyl, or a protecting group; and each $R_{14}$ is hydrogen, alkyl or aryl;

X is selected from the group consisting of O, $NR_9$, S, P, Se, $C_1$ to $C_6$ alkylene, SO, $SO_2$ and NH;

n is 0, 1, 2, 3, 4 or 5;

the method comprising steps of:

(a) providing a protected linear peptidomimetic compound of formula (IV)

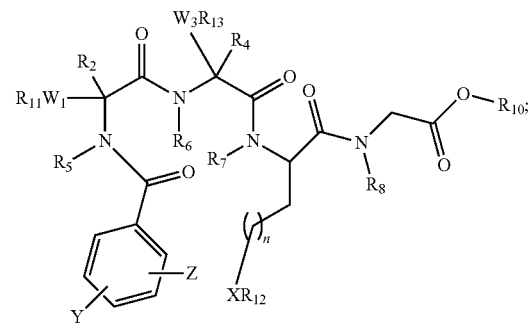

(IV)

wherein:

$R_2$, $R_4$, $R_5$, $R_6$ $R_7$ $R_8$, and $R_{10}$ have the meanings defined above;

$R_{11}$ and $R_{13}$ are independently hydrogen or a protecting group;

$R_{12}$ is a protecting group;

$W_1$ and $W_3$ are independently an amino acid side chain substituent of a natural or unnatural amino acid, less a hydrogen atom at the point of attachment to $R_{11}$ and $R_{13}$ respectively; and Z is selected from the group consisting of F, Cl, Br and I;

(b) selectively deprotecting the compound of formula (IV) to form a partially protected linear peptidomimetic compound of formula (III)

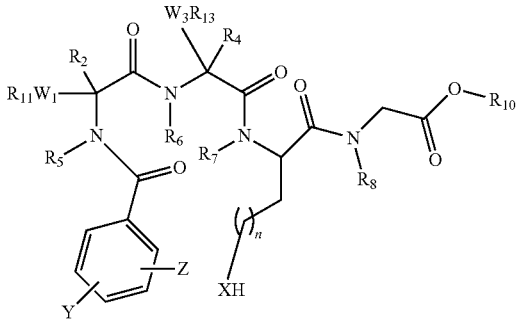

(III)

wherein:
R$_2$, R$_4$, R$_5$, R$_6$, R$_7$ R$_8$, R$_{10}$, R$_{11}$, R$_{13}$, W$_1$, W$_3$, X, Y, Z, and n have the meanings defined above;

(c) cyclizing the partially protected linear peptidomimetic compound of formula (III) to form a compound of formula (II) by an intramolecular aromatic nucleophilic substitution reaction

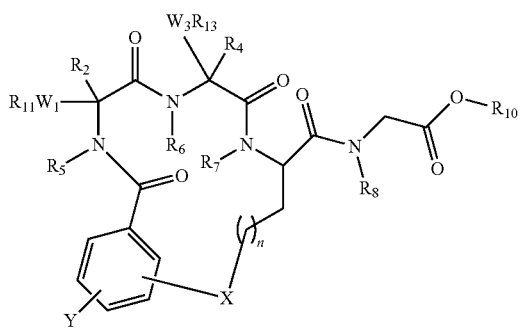

(II)

wherein:
R$_2$, R$_4$, R$_5$, R$_6$, R$_7$ R$_8$, R$_{10}$, R$_{11}$, R$_{13}$, W$_1$, W$_3$, X, Y, Z, and n have the meanings defined above;

(d) deprotecting an amino acid side chain protecting group in the compound of formula (II) to obtain the salt of the β-turn peptidomimetic cyclic compound of formula (I); and (e) crystallizing the β-turn peptidomimetic cyclic compound of formula (I) to obtain the crystalline salt of formula (I).

In certain embodiments, the disclosure provides a crystalline HCl salt of β-turn peptidomimetic cyclic compound of formula D3 and a method of preparing thereof.

DESCRIPTION OF THE DRAWINGS

The drawings illustrate generally, by way of example, but not by way of limitation, various embodiments discussed in the present document.

DETAILED DESCRIPTION OF THE INVENTION

Figure 1:
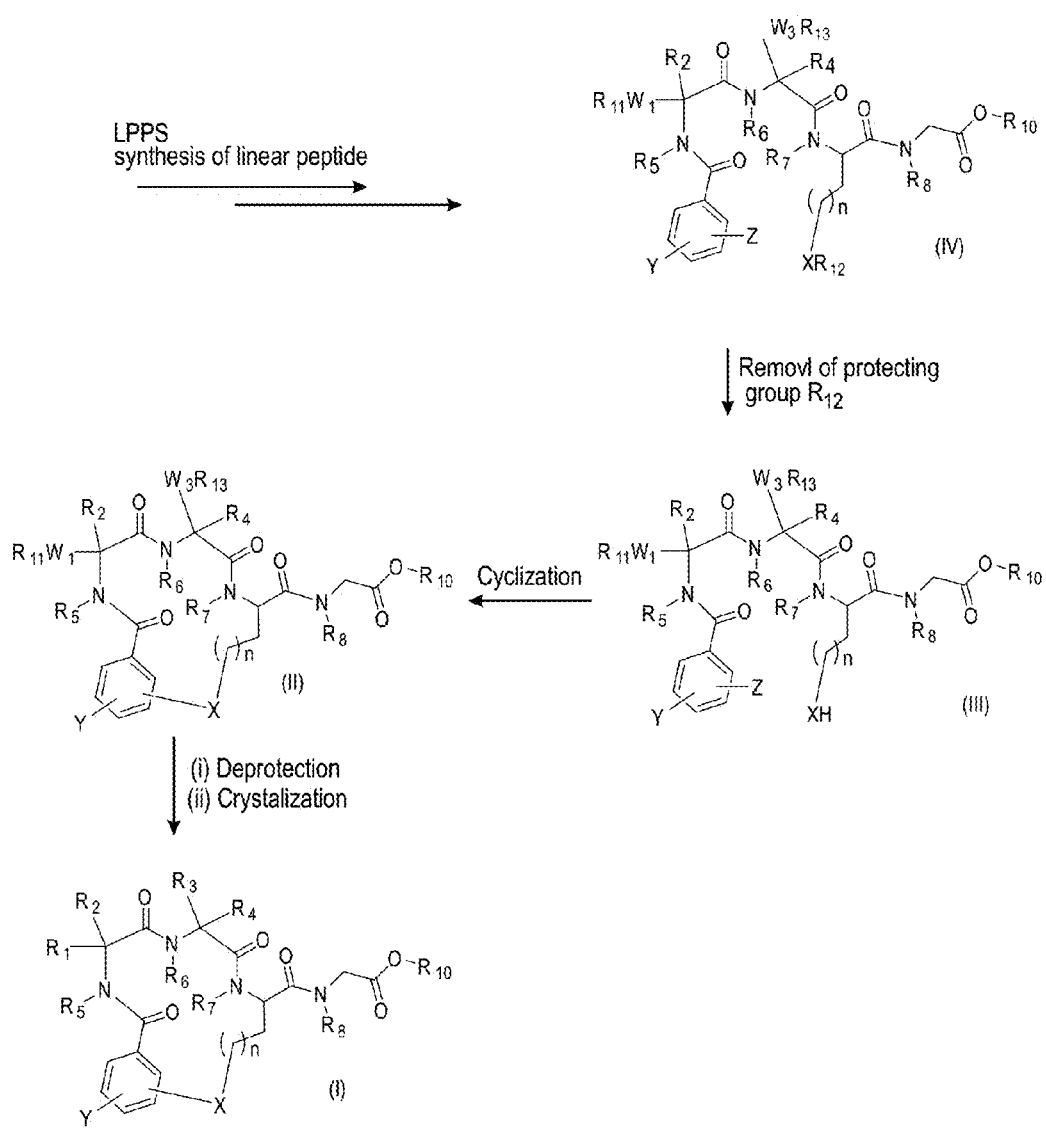
FIG. 1 is a general schematic illustration of the synthetic methods for preparing a crystalline form of a salt of β-turn peptidomimetic cyclic compound of formula (I) according to embodiments of the disclosure.

As used herein, the terms "a" or "an" are used, as is common in patent documents, to include one or more than one, independent of any other instances or usages of "at least one" or "one or more."

As used herein, the term "about" refers to an amount that is approximately, nearly, almost, or in the vicinity of being equal to or is equal to a stated amount.

As used herein, the term "crude" refers to a compound or a salt thereof that is less than 90% pure.

The purity of β-turn peptidomimetic cyclic compound or salt thereof is referred to by "percent purity." The measure of purity is not a measure of degree of crystallinity of the crystalline preparation. The purity may be measured by any means including nuclear magnetic resonance (NMR), gas chromatography/mass spectroscopy (GC/MS), liquid chromatography/mass spectroscopy (LC/MS), or high pressure liquid chromatography (HPLC).

A "crystal" refers to one or more crystals of a β-turn peptidomimetic cyclic compound or salt thereof. The determination of a crystal can be determined by any means including, optical microscopy, electron microscopy, x-ray powder diffraction, solid state nuclear magnetic resonance (SSNMR) or polarizing microscopy. Microscopy can be used to determine the crystal length, diameter, width, size and shape, as well as whether the crystal exists as a single particle or is polycrystalline.

A "crystalline" or a "crystalline form" refers to a compound that comprises crystals. In the present embodiments, a crystalline or a crystalline form of β-turn peptidomimetic cyclic compound or salt thereof comprises crystals of β-turn peptidomimetic cyclic compound or salt thereof. In one embodiment, a crystalline β-turn peptidomimetic cyclic compound or salt thereof may comprise some amount of amorphous β-turn peptidomimetic cyclic compound or salt thereof. In one embodiment, the crystalline β-turn peptidomimetic cyclic compound or salt thereof comprises more than 50% by weight of crystals of β-turn peptidomimetic cyclic compound or salt thereof. In another embodiment, the crystalline β-turn peptidomimetic cyclic compound or salt thereof comprises more than 60%, 70%, 80%, 90% or 95% by weight of crystals of β-turn peptidomimetic cyclic compound or salt thereof. The crystalline β-turn peptidomimetic cyclic compound or salt thereof may comprise 50-60%, 60-70%, 70-80%, 80-90% or 90-95% by weight of crystals of β-turn peptidomimetic cyclic compound or salt thereof. In another embodiment, the crystalline of β-turn peptidomimetic cyclic compound or salt thereof comprises more than 95% by weight of crystals of β-turn peptidomimetic cyclic compound or salt thereof, e.g., at least 96%, 97%, 98% or 99% by weight of crystals of β-turn peptidomimetic cyclic compound or salt thereof. or 100% by weight of crystals of β-turn peptidomimetic cyclic compound or salt thereof.

An "amorphous" form of a β-turn peptidomimetic cyclic compound or salt thereof refers to a β-turn peptidomimetic cyclic compound or salt thereof preparation that comprises few or no crystals of β-turn peptidomimetic cyclic compound or salt thereof. In one embodiment, an amorphous β-turn peptidomimetic cyclic compound or salt thereof comprises less than 20%, 10%, 5% or 1% by weight of crystals of β-turn peptidomimetic cyclic compound or salt thereof.

As used herein, the term "salts" refers to ionic compounds, which may act as precipitants.

As used herein, the term "pharmaceutically acceptable salt" refers to the acid addition salt compound formed with a suitable acid selected from an inorganic acid such as hydrochloric acid, hydrobromic acid; or an organic acid such as benzene sulfonic acid, maleic acid, oxalic acid, fumaric acid, succinic acid, p-toluenesulfonic acid and malic acid.

As used herein, the term "unnatural amino acid" refers to all amino acids which are not natural amino acids as described above. Such amino acids include the D-isomers of any of the 19 optically active and glycine naturally occurring amino acids described above. Unnatural amino acids also include homoserine, homocysteine, citrulline, 2,3-diaminopropionic acid, hydroxyproline, ornithine, norleucine, and thyroxine. Additional unnatural amino acids are well known to one of ordinary skill in the art. An unnatural amino acid may be a D- or L-isomer. An unnatural amino acid may also be an alpha amino acid, a beta amino acid or a gamma amino acid. An unnatural amino acid may also be a post-translationally modified amino acid, such as a phosphorylated serine, threonine or tyrosine, an acylated lysine, or an alkylated lysine or arginine. Many forms of post-translationally modified amino acids are known.

As used herein, the term "protecting group" means that a particular functional moiety, e.g., O, S, or N, is temporarily blocked so that a reaction can be carried out selectively at another reactive site in a multifunctional compound.

As used herein, the term "protic solvent" refers to a solvent that carries hydrogen attached to oxygen as in a hydroxyl group or attached to nitrogen as in an amine group. Such solvents can donate an H+(proton). Examples of protic solvents include water, ethanol, tert-butanol, and diethylamine.

As used herein, the term "aprotic solvent" refers to a solvent that carries few or no hydrogen attached to oxygen as in a hydroxyl group or attached to nitrogen as in an amine group.

As used herein, the term "ring" means a compound whose atoms are arranged in formulas in a cyclic form.

As used herein, the term "alkyl" means a hydrocarbon group that may be linear, cyclic, branched, or a combination thereof having the number of carbon atoms designated (i.e., $C_1$-$C_6$ means one to six carbon atoms). Examples of alkyl groups include methyl, ethyl, n-propyl, isopropyl, n-butyl, t-butyl, isobutyl, sec-butyl, pentyl, iso-amyl, hexyl, octyl, noyl and the like. Alkyl groups may be optionally substituted as defined herein. The term "alkylene," as used herein, refers to a saturated aliphatic group derived from a straight or branched chain saturated hydrocarbon attached at two or more positions, such as methylene (—$CH_2$—).

As used herein, the term "allyl" refers to compound containing the allyl group (i.e., $CH_2$=CH—$CH_2$—).

As used herein, the term "aryl" means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl. Aryl groups may be optionally substituted as defined herein. The term "arylene" designates any divalent group derived from aryl (such as above defined) by abstracting a hydrogen atom.

When a group is defined to be "null," this means that the group is absent.

When a group is substituted, the substituents may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, pyridinyl, thiophene, furanyl, lower carbamate, and lower urea.

For purposes of clarity and as an aid in understanding the invention, as disclosed and claimed herein, the following terms and abbreviations are defined below:

AcOH—acetic Acid
BAEA—bisaminoethylamine (diethylenetriamine)
Boc—t-butyloxycarbonyl
tBu—tert-butyl
Cbz—benzyloxycarbonyl
CTC—chlorotrityl chloride
DBU—1,8-Diazabicyclo[5.4.0]undec-7-ene
DCM—dichloromethane
DIC—1,3-Diisopropylcarbodiimide
DIPEA—N,N-diisopropylethylamine
DIPE—diisopropyl ether
DMF—dimethylformamide
EDC—N-ethyl-N'-(3-dimethylaminopropyl)-carbodiimide
EtOAc—ethyl acetate
Fmoc—9-fluorenylmethoxycarbonyl
FNBA—2-fluoro-5-nitro-benzoic acid
Glu—glutamic acid
Gly—glycine
HBTU—O-Benzotriazole-N,N,N',N'-tetramethyl-uronium-hexafluoro-phosphate
HSer—homoserine
HMPB-MBHA—4-Hydroxymethyl-3-methoxyphenoxybutirric acid MBHA, or 4-(4-hydroxymethyl-3-methoxyphenoxy)-butyryl-p-methyl-benzhydrylamine
HOBt—N-hydroxybenzotriazole
LPPS—liquid phase peptide synthesis
Lys—lysine
MeCN—acetonitrile
MeTHF—2-methyltetrahydrofuran
MTBE—methyl-tert-butyl ether
Mtt—methyltrityl
Pbf—pentamethyldihydrobenzofuransulfonyl
SPPS—solid phase peptide synthesis
TBAF—tetrabutylammonium fluoride
TBDMS—tert-butyldimethylsilane
tBu—tert-Butyl ester
TFA—trifluoroacetic acid
THF—tetrahydrofuran
TIS—triisopropylsilane
TMG—tetramethylguanidine
Trt—trityl FIG. 1 shows Scheme 1, depicting general routes to prepare a crystalline form of a salt of a β-turn peptidomimetic cyclic compound of formula (I), including the steps of: (a) providing a protected linear peptidomimetic compound of formula (IV); (b) selectively deprotecting the compound of formula (IV) to form a partially protected linear peptidomimetic compound of formula (III); and (c) cyclizing the partially protected linear peptidomimetic compound of formula (III) to form a compound of formula (II) by an intramolecular aromatic nucleophilic substitution reaction; and (d) deprotecting an amino acid side chain protecting group in the compound of formula (II) to obtain the salt of the β-turn peptidomimetic cyclic compound of formula (I); and (e) crystallizing the salt of the β-turn peptidomimetic cyclic compound of formula (I) to obtain the compound of formula (I) in crystalline form.

In certain embodiments, the invention provides a method of preparing a crystalline β-turn peptidomimetic cyclic salt of formula (I) having a macrocyclic ring of from 14 to 16 ring atoms.

In certain embodiments, the method provides compounds where $R_1$ and $R_3$ are amino acid side-chain substituents. Typically, $R_1$ and $R_3$ are independently derived from natural or unnatural amino acids. For example, $R_1$ and $R_3$ can independently be derived from the twenty naturally occurring protein amino acids (natural), or modified amino acids (unnatural), in either enantiomeric configuration. The twenty natural amino acids are alpha-amino acids which include glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met). The generic structure of an alpha-amino acid is illustrated by Formula A: $H_2NCH(R^*)COOH$. $R^*$ represents the side chain substituent of the amino acid, which refers to as either $R_1$ or $R_3$ in the present disclosure.

An unnatural amino acid typically is any structure having Formula A wherein the $R^*$ group is any substituent other than one used in the twenty natural amino acids. See for instance, Biochemistry by L. Stryer, 31(1 ed. 1988), Freeman and Company, New York, for structures of the twenty natural amino acids. Unnatural amino acids also can be naturally occurring compounds other than the twenty alpha-amino acids above.

Such unnatural amino acids include the D-isomers of any of the 19 optically active and glycine naturally occurring amino acids described above. Unnatural amino acids also include homoserine, homocysteine, 2,3-diaminopropionic acid, citrulline, hydroxyproline, ornithine, norleucine, and thyroxine. Additional unnatural amino acids are well known to one of ordinary skill in the art. An unnatural amino acid may be a D- or L-isomer. An unnatural amino acid may also be a beta amino acid or a gamma amino acid having Formula B: $H_2N(CH)_n(R^*)COOH$ wherein n is equal to 2 or 3 and $R^*$ represents the side chain substituent of any of the twenty proteinogenic amino acids or any substituent other than one used in the twenty natural amino acids. An unnatural amino acid may also be a post-translationally modified amino acid, such as a phosphorylated serine, threonine or tyrosine, an acylated lysine, or an alkylated lysine or arginine. Many forms of post-translationally modified amino acids are known.

In certain embodiments, the method provides compounds where $R_1$ and $R_3$ are independently a side chain substituent of two different amino acids. In certain of such embodiments, $R_1$ and $R_3$ are independently a side chain substituent of lysine, glutamic acid, tyrosine, isoleucine, asparagine, arginine or threonine. In certain embodiments, $R_1$ and $R_3$ are independently a side chain substituent of glutamic acid, lysine, isoleucine or arginine. In one embodiment, $R_1$ and $R_3$ are independently a side chain substituent of glutamic acid or lysine. In another embodiment, $R_1$ and $R_3$ are independently a side chain substituent of isoleucine or arginine.

In general, the amino acid side-chain substituents ($R_1$ and $R_3$) are protected by suitable protecting groups ($R_{11}$ and $R_{13}$, respectively) prior to the cyclization step in the method of preparing β-turn cyclic peptidomimetic compounds of the disclosure. When the amino acid side-chain substituents, $R_1$ and $R_3$, are protected, they are represented as $W_1R_{11}$ and $W_3R_{33}$ respectively, where $W_1$ and $W_3$ are independently an amino acid side chain substituent of a natural or unnatural amino acid, less one hydrogen atom at the point of attachment to $R_{11}$ and $R_{13}$, respectively. The one hydrogen atom is usually found in a functional group such as carboxylic acid, amine, thiol, amide, hydroxyl and guanidine of the amino acid side-chain substituents.

Amino acid side-chain protection of any other sensitive reactive groups of any molecule involved in the synthesis at any step of the method described in the disclosure can be achieved by means of conventional protecting groups such as those described by T. W. Greene & P. G. M. Wuts (Protective Groups In Organic Synthesis 1991, John Wiley and Sons, New-York); and by Sewald and Jakubke (Peptides: chemistry and Biology, 2002, Wiley-VCH, Wheinheim p. 142). For example, alpha amino protecting groups include, but are not limited to, acyl type protecting groups (e.g., trifluoroacetyl, formyl, acetyl), aliphatic urethane protecting groups (e.g., t-butyloxycarbonyl (Boc), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl).

Amino acids side chain protecting groups may include tert-butyl ether for serine, threonine, and tyrosine; Boc for lysine, tryptophan, and histidine; trityl for serine, threonine asparagine, glutamine, cysteine and histidine; tert-butyl or allyl ester for aspartate and glutamate, Pbf for arginine; benzyl for threonine and serine; Cbz for tyrosine, threonine, serine, arginine, and lysine; alkyl silane for serine and threonine; and all other protecting groups known in the art.

In certain embodiments, the method provides compounds where $R_{11}$ and $R_{13}$ are independently selected from the group consisting of trifluoroacetyl, formyl, acetyl, t-butyloxycarbonyl (BOC), cyclohexyloxycarbonyl, fluorenyl-9-methoxy-carbonyl (Fmoc), benzyloxycarbonyl (Cbz), Cbz derivatives, triphenyl, methyl, benzyl, allyloxycarbonyl, tert-butyl, alkyl silane and allyl.

In certain embodiments, the method provides compounds where $R_1$ is a side chain substituent of glutamic acid, and $R_{11}$ is allyl or tert-butyl. In certain of such embodiments, $R_1$ is a side chain substituent of glutamic acid, and $R_{11}$ is tert-butyl.

In certain embodiments, the method provides compounds where $R_3$ is a side chain substituent of lysine and $R_{13}$ is benzyloxycarbonyl, allyloxycarbonyl, or tert-butyloxycarbonyl (BOC). In certain of such embodiments, $R_3$ is a side chain substituent of lysine and $R_{13}$ is tert-butyloxycarbonyl (BOC).

The protecting groups may be removed at a convenient subsequent stage using methods known in the art. In certain embodiments, the protecting groups of the amino acid side chains $R_1$ and $R_3$ are not removed under the same condition used to cleave the peptidomimetic compound from the solid support. In certain of such embodiments, the protecting groups of the amino acid side chains $R_1$ and $R_3$ are not removed under the same acidic condition used to cleave the peptidomimetic compound from the solid support.

In certain embodiments, the method provides compounds where $R_2$ and $R_4$ are independently hydrogen or $C_1$ to $C_6$ alkyl.

In certain embodiments, the method provides compounds where $R_5$, $R_6$ and $R_7$ are hydrogen.

In certain embodiments, the method provides compounds where $W_1$ and $W_3$ are independently a side chain substitutent of two different amino acids, less a hydrogen atom on the functional group. In certain embodiments, $W_1$ and $W_3$ are independently a side chain substitutent of lysine, glutamic acid, tyrosine, isoleucine, asparagine, arginine or threonine, less a hydrogen atom on the functional group. In certain embodiments, $W_1$ and $W_3$ are independently a side chain substitutent of glutamic acid or lysine. In certain embodiments, $W_1$ and $W_3$ are independently a side chain substitutent of isoleucine or arginine. In certain embodiments, $W_1$ is a side chain substitutent of glutamic acid, less a hydrogen atom on the functional group, and $R_{11}$ is allyl or tert-butyl. In certain embodiments, $W_3$ is a side chain substitutent of lysine and $R_{13}$ is benzyloxycarbonyl, allyloxycarbonyl, or tert-butyloxycarbonyl (BOC).

In certain embodiments, the method provides compounds where Y is attached to the benzene ring of the formulas at the meta position relative to the point of attachment of the amide group. In certain embodiments, Y is —$NO_2$.

In certain embodiments, the method provides compounds where Z is attached to the benzene ring of the formulas at the ortho position relative to the point of attachment of the amide group. In certain embodiments, Z is F.

In certain embodiments, the method provides compounds where n is 1.

In certain embodiments, the terminal functional group X may be protected (i.e., when $R_{12}$ is a protecting group). In certain embodiments, when X is O and $R_{12}$ is trityl (Trt), tert-butyldimethylsilane (TBDMS), or any protecting group that can be removed under conditions that do not cause deprotection of the other protecting groups present in the formula, such as mild acidic conditions. In certain of such embodiments, when X is O and $R_{12}$ is trityl (Trt), or tert-butyldimethylsilane (TBDMS). In certain embodiments, X is S and $R_{12}$ is trityl. In certain embodiments, X is NH and $R_{12}$ is 4-methyltrityl (Mtt).

Partial Deprotection

The protecting group $R_{12}$ may be removed by treating the protected linear peptidomimetic compound of formula (IV) with a mild acidic solution, such as a solution containing from about 0.01% to about 50% (v/v), from 0.1% to 10% (v/v), from 0.5% to 5% (v/v), or from 2% to 5% (v/v) of an acid, such as, trifluoro acetic acid (TFA), or acetic acid (e.g., 50%-95%, or 60%-90% (v/v)). The functional amino acid side chains are protected using more stable protecting groups that are not cleaved or deprotected under such mild acidic conditions. Such functional amino acid side chains can be protected with a strong acid labile protecting group on the functional groups. The protecting groups used on the functional amino acid side chains are described herein. Thus, the removal of the protecting group $R_{12}$ does not cause significant deprotection of any protected functional group $R_{11}$ and $R_{13}$ present in formula (IV).

The removal of the protecting group $R_{12}$ may be carried out in different solvent systems. The solvent system is an organic solvent or a mixture of organic solvents. The solvent system may comprise a polar, aprotic solvent, such as, dichloromethane, acetonitrile or tetrahydrofurane and mixture thereof.

A scavenger can be added to the mild acidic solution to prevent the alkylation of the X group by the alkyl-carbenium ion formed during the reaction. Suitable scavengers include, but are not limited to, triisopropylsilane (TIS), thioanisol, trialkylsilane (e.g., trimethylsilane, triethylsilane), or mixture thereof. In one embodiment, the scavenger is triisopropylsilane (TIS).

In certain embodiments, the mild acidic solution contains less than 10%, 5%, or 3% of a mixture of acid and scavenger. The relative ratio by volume of acidic material to scavenger in the mild acidic solution used in the removal of the protecting group $R_{12}$ can be from about 1:1 to about 1:5, from about 1:1 to about 1:3, or about 1:2. In one embodiment, the removal of the protecting group $R_{12}$ is performed in a solution comprising less than 10% of a mixture of TFA and TIS in a ratio by volume of from about 1:1 to about 1:5.

Cyclization

The cyclization reaction may be carried out via an aromatic nucleophilic substitution reaction by the nucleophile X.

The cyclization reaction may be performed in polar aprotic solvents, such as, acetonitrile, tetrahydrofurane (THF), dioxanes, or mixtures thereof. In one embodiment, the cyclization reaction is performed in THF. Significant amounts of solvents like water and methanol are to be avoided as they can act as nucleophiles and interfere with the cyclization. In one embodiment, the cyclization reaction is performed in less than about 0.5% of water, or in the absence of water. In one embodiment, the cyclization reaction is performed in less than about 0.5% of methanol, or in the absence of methanol. In one embodiment, the cyclization reaction is performed in less than about 0.5% of water and in less than about 0.5% of methanol.

In certain embodiments, the cyclization reaction is a base-catalyzed cyclization reaction. The role of the base in the cyclization reaction is to increase the nucleophilic character of the functional group X. Examples of bases that can be used are t-BuOK, $CsCO_3$, $K_2CO_3$, or mixtures thereof.

An important aspect of the cyclization step is to control the concentration of the partially protected linear peptidomimetic intermediate (III) during the reaction to avoid the formation of the dimeric side product. When the cyclization reaction is performed at higher concentrations of the partially protected linear peptidomimetic intermediate (III), e.g., greater than 0.05 M, the rate of intermolecular reaction increases, and thus accelerates the rate of dimeric side product formation. Consequently, to avoid the formation of dimers, the cyclization reaction may be performed at concentrations lower than 0.05 M, particularly, at concentrations lower than 0.03 M, or at concentrations lower than 0.02 M. Such low concentrations (i.e., high dilutions) may be achieved by using large volumes of solvents. Alternatively, the cyclization reaction may be performed by slow addition of the partially protected linear peptidomimetic intermediate (III) to the reaction media, which can avoid the usage of large volumes of solvent.

The cyclization reaction may be carried out at a temperature from −20° C. to 15° C., from −10° C. to 5° C., or from −8° C. to −1° C. Reaction time at room temperature can vary from 5 minute to 5 hours according to ring size, nucleophile involved in the reaction, base and solvent. In certain embodiments, the cyclization reaction time at room temperature is from about 5 minutes to about 1 hour, from about 5 minutes to about 30 minutes, or from about 15 minutes to about 20 minutes.

The reaction can be monitored by analytical HPLC, LC-MS or UV as the partially protected linear peptidomimetic intermediate (III) and the β-turn peptidomimetic cyclic compound of formula (I) have different retention time, mass, and UV profiles.

Once the cyclization is completed, an acid solution may be added to the reaction mixture to neutralize the reaction mixture. Suitable acid includes HCl, $KHSO_4$, AcOH. For example, an aqueous acid solution may be used. The concentration of the acid solution may vary from about 0.1 M to about 1 M, or from about 0.05 N to about 0.2 N. Subsequently, the organic solvent may be removed, e.g., by evaporation, to obtain a crude residue slurry.

Alternatively, the crude residue slurry may be filtered to collect the crude. The residue or filter may be washed with a solvent, e.g., DIPE or mixture thereof.

The crude product can be slurried in EtOAc at 40° C. for 30-40 min, cooled to 0° C., and filtered to collect the product.

Deprotection

For the final deprotection of the amino acids side chain protecting groups, the protected β-turn peptidomimetic cyclic compound of formula (IV) is treated with appropriate reagents according to the type of protecting groups present in the formula. In certain embodiments an acidic solution is used. In some embodiments, the acidic solution includes a HCl solution with a concentration of from 10% to 60%, from 20% to 50% or from 30% to 40%. HCl can be dissolved in water or in organic solvents, such as acetonitrile. In one embodiment, the acidic solution includes a concentrated HCl solution, (e.g., 30-40%) and acetonitrile.

The final deprotection may be performed at a temperature of from about 5° C. to about 25° C., from about 10° C. to about 20° C., or from about 12° C. to about 17° C. In certain embodiments, the protected β-turn peptidomimetic cyclic compound of formula (IV) may be suspended in an acidic solution at a temperature of from about 5° C. to about 25° C., from about 10° C. to about 20° C., or from about 12° C. to about 17° C. (e.g., at about 15° C.).

Crystallization

In certain embodiments, the β-turn peptidomimetic cyclic compound of formula (I) may be crystallized or precipitated via a basification-acidification method. The basification-acidification method includes the steps of: contacting the compound or salt of formula (I) with a basic solution in water having a basic pH, and reducing the pH to obtain an acidic pH to precipitate or crystallize the compound or salt of formula (I).

The compound of formula (I) may be treated with an aqueous basic solution containing an inorganic base, such as NaOH, LiOH, KOH, $Mg(OH)_2$ or mixtures thereof. The basic solution may be heated to a temperature of from about 30° C. to about 70° C., or from about 40° C. to about 60° C. The concentration of the basic solution may be from about 0.1 M to about 5 M, from about 1 M to about 3 M, or from about 1.5 M to about 2 M. Typically, from about 2 to about 8 equivalents, from about 3 to about 7 equivalents, or from about 3 to about 5 equivalents of the inorganic base relative to the crude final product (i.e., formula (I)) may be used. The basic pH may be from about 9 to about 12, from about 9 to about 11, from about 8 to about 12.

The method may further include a step of filtering the basic solution containing the compound of formula (I) prior to reducing the pH of the basic solution. The purpose of the filtering is to remove any insoluble materials. The filtering may be performed at a temperature above room temperature, e.g., from about 40° C. to about 70° C., or from about 45° C. to about 60° C.

The filtrate or the basic solution mixture may be acidified by admixing the basic solution with an acid to achieve an acidic pH of from about 0 to about 4, from about 0 to about 3, or from about 0 to about 2. An inorganic acid may be used to acidify the basic solution. Examples of inorganic acid include, but are not limited to HCl, HBr, nitric acid, sulfuric acid, phosphoric acid or mixtures thereof. Typically, from about 3 to about 9 equivalents, from about 4 to about 8 equivalents, or from about 5 to about 7 equivalents of the acid may be used relative to the crude final product of formula (I).

The crystals of the salt of formula (V) can be formed or precipitated from the acidified solution. The acidic pH may promote the formation of a gel, subsequently transforming into a slurry/cloudy solution that contains crystals. Too less acid may slow down the transformation from gel to slurry. Typically, from about 3 to 7 equivalents, from about 4 to 6 equivalents, or about 5 equivalents of acid relative to the crude final product (i.e., formula (I)) may be used. In certain embodiments, a minimum of 2 equivalents excess of acid relative to base is required to promote the crystallization of the compound of formula (IV). Once the needles crystals (form V) are formed, they are stable in the slurry and can be stored in room temperature for at least 3 weeks.

To facilitate the growth or precipitation of crystals with the minimal amount of impurity formation, the acidified solution may be agitated or stirred for a period of time and/or kept under a temperature of from about 0° C. to about 60° C. During the crystallization process, samples may be taken from the acidified solution and monitored for crystal or precipitate formation by microscopic examination and the yield may be followed spectrophotometrically (e.g., HPLC). To avoid formation of impurities and to facilitate growth or precipitation of crystals during the formation of crystals, a temperature profile may be used during crystallization. That is, the acidified solution may be agitated under one or more temperature ranges each for a specific period of time. For example, the one or more temperature may include a first temperature, a second temperature, a third temperature and so forth, and each temperature can be chosen, independently, from any of the following temperature ranges: from about 0° C. to about 30° C., from about 0° C. to about 20° C., from about 0° C. to about 10° C., from about 10° C. to about 40° C., from about 10° C. to about 30° C., from about 10° C. to about 20° C., from about 20° C. to about 50° C., from about 20° C. to about 40° C., from about 20° C. to about 30° C., from about 30° C. to about 60° C., from about 30° C. to about 50° C., from about 30° C. to about 40° C., from about 40° C. to about 70° C., from about 40° C. to about 60° C., from about 40° C. to about 50° C., from about 50° C. to about 70° C., from about 50° C. to about 60° C., etc. The acidified solution may be agitated for a period of time at each temperature range, and each period of time can be chosen, independently, from any of the following time ranges: for at least 5, 10, 15, or 60 minutes or for duration of 1, 2, 3 hours, and so forth, and up to 1 month. In certain embodiments, the agitation period of time may be from about 5 minutes to about 20 hours, from about 15 minutes to about 15 hours, from about 30 minutes to about 10 hours, from about 1 hour to about 5 hours, from about 2 hours to about 4 hours, etc.

The method of the disclosure may produce in a yield of at least about 30 mole %, or from about 35 to about 45 mole %. These yields are based on the moles of the limiting reactant, for instance, the moles of the HSer compound.

In one specific aspect, the disclosure provides a crystalline HCl salt of β-turn peptidomimetic cyclic compound of formula D3, also referred to herein simply as "D3" and the method of preparing thereof. The structure of the HCl salt of D3 is shown below:

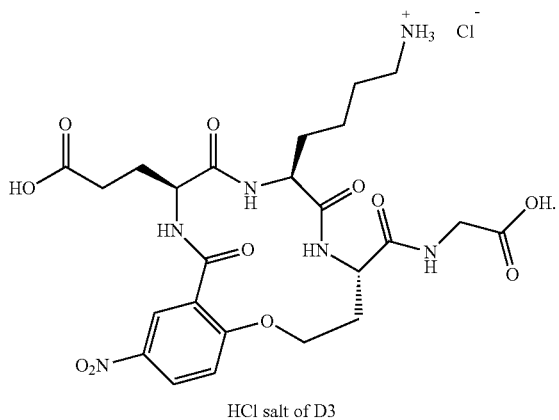 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O ; Cl]

HCl salt of D3

Figure 2:
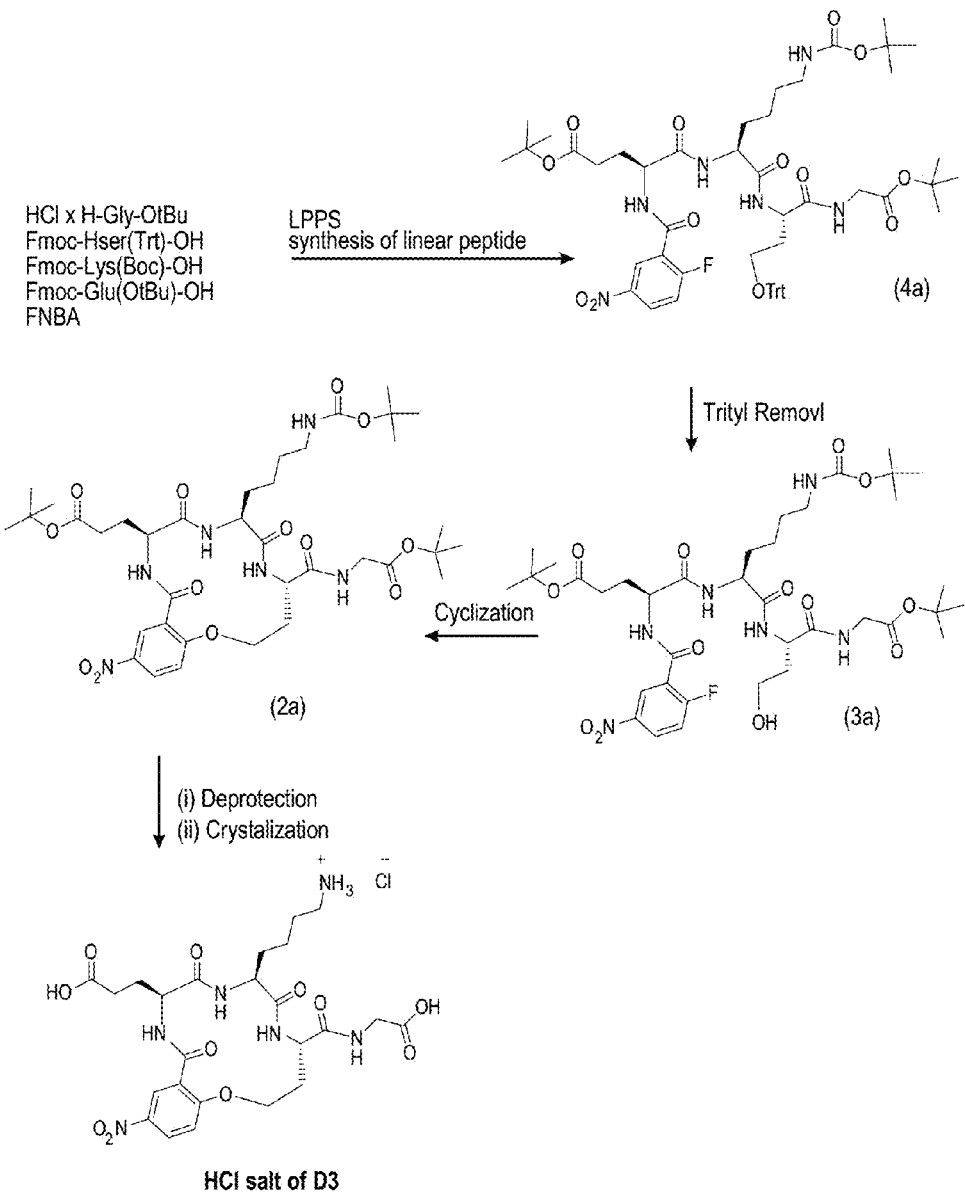
FIG. 2 is an exemplary reaction scheme for preparing a crystalline form of a HCl salt of β-turn peptidomimetic cyclic compound of structure D3 according to an embodiment of the disclosure.

FIG. 2 shows exemplary reaction scheme (Scheme 2) which depicts a route to prepare a crystalline HCl salt of the β-turn peptidomimetic cyclic compound of formula D3.

In embodiments, the present disclosure provides a method of preparing a crystalline form of a HCl salt of a β-turn peptidomimetic cyclic compound having the following structure:

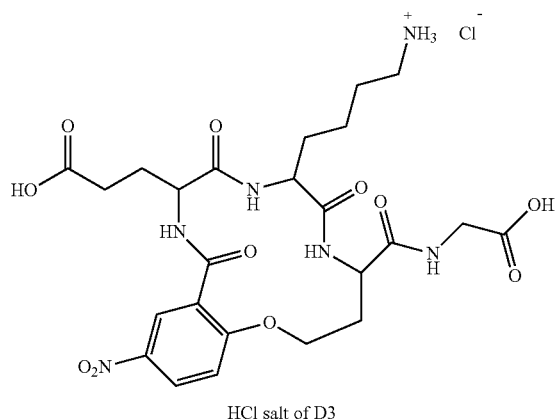 [SMILES: NCCCCC1NC(=O)C(CCC(=O)O)NC(=O)c2cc([N+](=O)[O-])ccc2OCCC(C(=O)NCC(=O)O)NC1=O ; Cl]

HCl salt of D3 the method comprising steps of:
(a) providing a protected linear peptidomimetic compound of formula (4a);

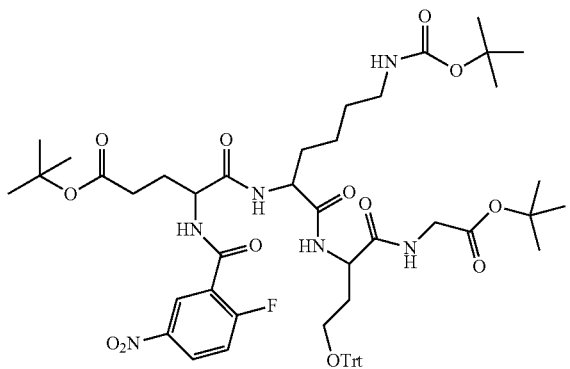

(4a)

(b) selectively deprotecting the compound of formula (4a) to form a partially protected linear peptidomimetic compound of formula (3a);

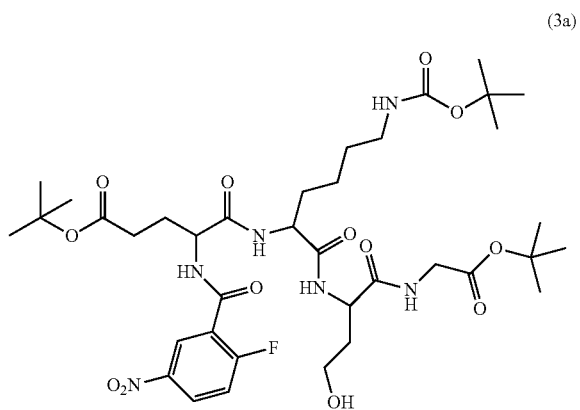 [SMILES: CC(C)(C)OC(=O)CCC(NC(=O)c1cc([N+](=O)[O-])ccc1F)C(=O)NC(CCCCNC(=O)OC(C)(C)C)C(=O)NC(CCO)C(=O)NCC(=O)OC(C)(C)C]

(3a)

(c) cyclizing the partially protected linear peptidomimetic compound of formula (3a) to form a compound of formula (2a) by an intramolecular aromatic nucleophilic substitution reaction;

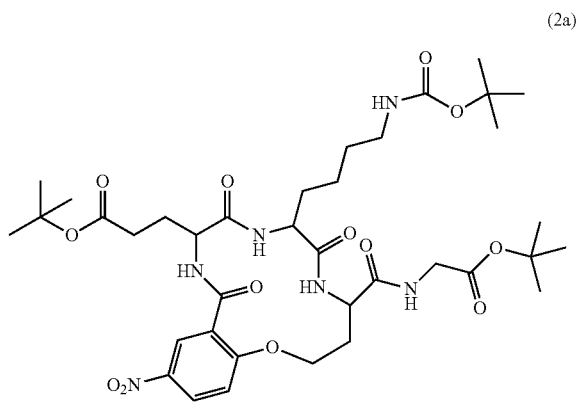 [SMILES: CC(C)(C)OC(=O)CCC1NC(=O)c2cc([N+](=O)[O-])ccc2OCCC(C(=O)NCC(=O)OC(C)(C)C)NC(=O)C(CCCCNC(=O)OC(C)(C)C)NC1=O]

(2a)

(d) deprotecting an amino acid side chain protecting group in the compound of formula (II) to obtain HCl salt of D3; and (e) crystallizing HCl salt of D3 to obtain the HCl salt of D3 in crystalline form.

In embodiments, the protected linear peptidomimetic compound of formula (4a) may be obtained from a liquid phase peptide synthesis process comprising the step of coupling Fmoc-Hser(Trt)-OH with H-Gly-OtBu.HCl thereby forming a dipeptide Fmoc-Hser(Trt)-Gly-OtBu. The process may further comprising the step of coupling the dipeptide H-Hser(Trt)-Gly-OtBu with Fmoc-Lys(Boc)-OH thereby forming a tripeptide Fmoc-Lys(Boc)-Hser(Trt)-Gly-OtBu. The process may further comprising the step of coupling the tripeptide H-Lys(Boc)-Hser(Trt)-Gly-OtBu with Fmoc=Glu(Otbu)-OH thereby forming a tetrapeptide Fmoc-Glu(OtBu)-Lys(Boc)-Lys(Boc)-Hser(Trt)-Gly-OtBu.

One of more of the coupling steps may be performed in the presence of diisopropylamine (DIPEA) and a condensation reagent, such as O-(7-azabenzotriazol-1-yl)-N,N,N',N'-tetramethyl-uronium-tetrafluoroborate (HATU), 1-[3-(dimethylamino)propyl]-3-ethylcarbodiimide hydrochloride (EDC.HCl), O-benzotriazol-N,N,N',N'-tetramethyl-uronium-hexafluoro-phosphate (HBTU), 1-hydroxybenzotriazole (HOBt), benzotriazol-1-yl-oxy-tris-pyrrolidino-phosphoniumhexafluoro phosphate (PyBOP), 1-hydroxy-7-azabenzo triazole, TBTU ((Benzotriazolyl) tetramethyluronium tetrafluoroborate), TATU ((7-Azabenzotriazolyl) tetramethyluronium tetrafluoroborate) and COMU ((1-Cyano-2-ethoxy-2-oxoethylidenaminooxy)dimethylamino-morpholino-carbenium hexafluorophosphate), Oxyma [ethyl 2-cyano-2-(hydroxyimino)acetate], K-Oxyma (2-Cyano-2-(hydroxyimino)acetic acid ethyl ester, potassium salt) or mixtures thereof. In one embodiment, the condensation reagent is EDC.HCl/HOBt. The coupling step of Fmoc-Hser(Trt)-OH with H-Gly-OtBu.HCl may be performed in the presence of DIPEA and EDC.HCl/HOBt. The coupling step of the dipeptide H-Hser(Trt)-Gly-OtBu with Fmoc-Lys(Boc)-OH may be performed in the presence of DIPEA and EDC.HCl/HOBt. The coupling step of the tripeptide H-Lys(Boc)-Hser(Trt)-Gly-OtBu with Fmoc-Glu (Otbu)-OH may be performed in the presence of DIPEA and EDC.HCl/HOBt.

The step of removing the N-terminal Fmoc protecting group of any of the peptides may be performed in the presence of BAEA to provide an N-terminal free amino group.

In certain embodiments, the crystalline form of the disclosure comprises crystalline form IV, form V or mixtures thereof. These crystalline forms can be produced by the methods described herein and are substantially free of other crystalline forms (i.e., other than form IV or form V). The term "substantially free" refers to an amount of 10% or less of another form, for example 8%, 5%, 4%, 3%, 2%, 1%, 0.5%, or less of another form. The crystalline form of the disclosure can be characterized by X-Ray powder diffraction (XRPD), thermal data by differential scanning calorimeter (DSC) and thermal gravimetric analysis (TGA), dynamic vapor sorption (DVS), and/or gravimetric vapor sorption (GVS).

In one embodiment, the disclosure provides a crystalline form IV of a HCl salt of the β-turn peptidomimetic cyclic compound of formula D3. In one embodiment, the disclosure provides a crystalline form V of a HCl salt of the β-turn peptidomimetic cyclic compound of formula D3. In one embodiment, the disclosure provides a crystalline form including a mixture of form IV and form V of a HCl salt of the β-turn peptidomimetic cyclic compound of formula D3.

In certain embodiments, the form IV is hygroscopic. In certain embodiments, the crystalline form IV may have a weight increase of from about 10% to about 30% at relative humidity (RH) from 60% to 100%, where the weight increase is due to the weight gain of water content. In certain embodiments, the absorption or desorption of water process in the crystalline form may be reversible. In certain embodiments, the crystalline form IV has an irregular shape. In certain embodiments, the crystalline form V is in needle shaped form.

The transformation of the crystalline forms (between form IV and form V) of the disclosure occurs when varying RH. For example, form IV may be transformed to form V when exposed to high relative humidity, such as from 75% to 100%, from 85% to 100%, or from 95% to 100% RH. Form IV may be transformed to form V when treated with an acidic solution, e.g., an aqueous solution of hydrochloric acid, where the concentration of hydrochloride acid from about 0.001M to about 0.5M, from about 0.01M to about 0.2M, from about 0.05M to about 0.1M. Form IV may be transformed to a mixture of form V and some other forms when treated in a very dilute acidic solution, e.g., having a concentration of lower than 0.001M, or pure water (i.e., in the absence of acid or base). Form V may be transformed back to form IV upon drying. The rate of the transformation may be dependent on the concentration of the acidic solution. Generally, the rate of transformation from form V to form IV is faster when the crystalline form V is treated with a higher concentration of acidic solution.

In certain embodiments, the crystalline salt of the β-turn peptidomimetic cyclic compound of formula D3 contains needle shaped crystals.

In certain embodiments, the crystalline form of a salt of a β-turn peptidomimetic cyclic compound of formula D3 is obtained from a solution containing at least 60% water.

In certain embodiments, the crystalline form of a salt of a β-turn peptidomimetic cyclic compound of formula D3 is a hydrate.

In certain embodiments, the crystalline form of the HCl salt of D3 is characterized by an XRPD pattern with characteristic peaks at diffraction angles (° 2theta) of 6.7±0.2 and 9.1±0.2. In one embodiment the crystalline form of the HCl salt of D3 is characterized by an XRPD pattern with characteristic peaks at diffraction angles (° 2theta) of 6.7±0.2, 9.1±0.2, 4.4±0.2, 5.1±0.2 and 2.6±0.2.

In one embodiment the crystalline form of the HCl salt of D3 is characterized by an XRPD pattern with having two or more, three or more, four or more, or five or more characteristic peaks at diffraction angles (° 2theta) selected from 6.7±0.2, 9.1±0.2, 4.4±0.2, 5.1±0.2, 2.6±0.2, 11.5±0.2, 15.3±0.2, 16.6±0.2, 17.7±0.2, 18.2±0.2, 20.2±0.2, 21.6±0.2, 22.1±0.2, 22.5±0.2, 23.2±0.2, 24.1±0.2.

Figure 13A:
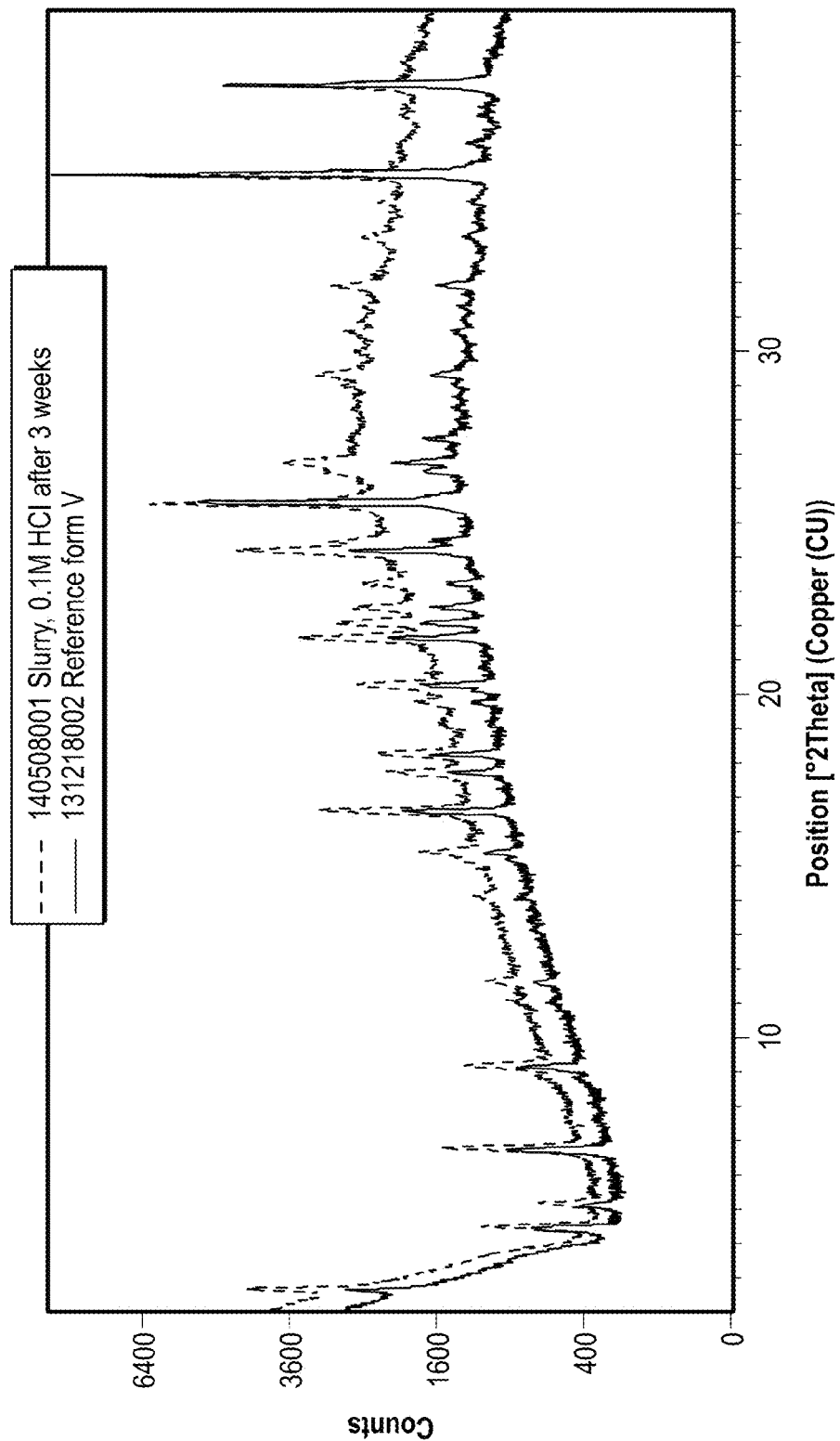
FIG. 13*a* is a result of the XRPD analysis of a crude D3 HCl salt slurry in 0.1M HCl solution after 3 weeks for stability check (top curve), and a reference D3 HCl salt crystalline form V (bottom curve).
Figure 13B:
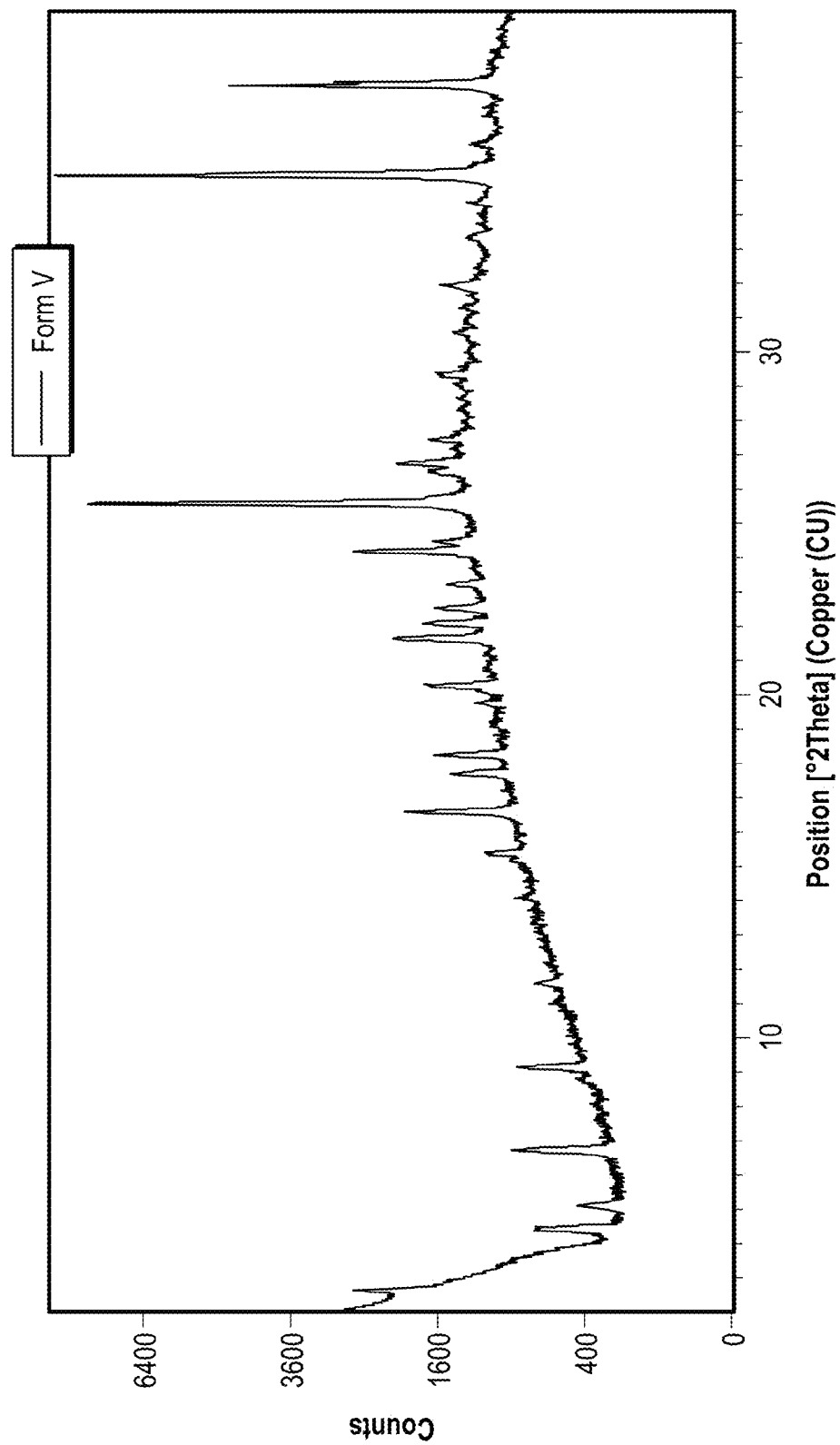
FIG. 13*b* is a result of the XRPD analysis of a reference D3 HCl salt crystalline form V.

In one embodiment of this aspect, there is provided a crystal form of which has a powder X-ray diffraction pattern essentially as set out in FIG. 13b.

EXAMPLES

The following examples are merely illustrative of the disclosure and should not be considered limiting the scope of the invention in any way, as these examples and other equivalents thereof will become apparent to those skilled in the art in light of the present disclosure and the accompanying claims. All percentages used in the application are percent weight by weight (w/w) unless otherwise noted.

Example 1

FIG. 2 (Scheme 2) illustrates the synthesis of a HCl salt of D3, which is one embodiment of β-turn peptidomimetic cyclic compound of formula (I).

Synthesis of Compound 4a can be carried out by standard stepwise LPPS (liquid phase peptide synthesis) procedures. See for example, L. A. Carpino et al., Organic Process Research & Development 2003, 7, 28-37)

(a) Synthesis of Dipeptide H-Hser(Trt)-Gly-OtBu

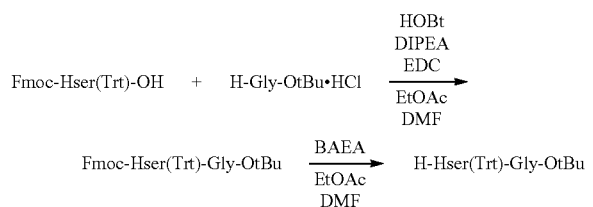

To a vessel containing Fmoc-Hser(Trt)OH (37.5 g), HCl× H-GlyOtBu (12 g) and HOBt (10.8 g) were added EtOAc (227 ml) and DMF (45 ml). The mixture was agitated at 5° C. DIPEA (12.5 ml) and EDC×HCl (15 g) were added. The mixture was agitated at 20° C. to complete conversion (normally <2 h). On completion, the reaction mixture was washed twice with NaCl (23%, 113 ml). It was made sure that no aqueous phase was left behind in the reactor, and that no part of the organic layer was discarded after washings.

To the organic solution were added DMF (45 ml) and BAEA (34.5 ml). The mixture was agitated at 20° C. for 30 min for complete removal of the Fmoc group. On completion, the reaction mixture was extracted with NaCl (23%, 113 ml) once, and with NaHCO$_3$ (4.8%, 113 ml) twice. The organic solution was ready for next coupling. It was made sure that no aqueous phase was left behind in the reactor, and that no part of the organic layer was discarded after washings.

(b) Synthesis of Tripeptide H-Lys(Boc)-Hser(Trt)-Gly-OtBu

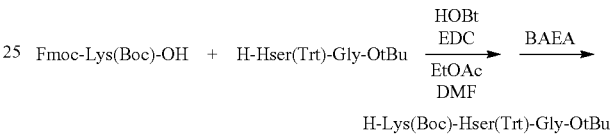

The organic solution containing the dipeptide was diluted with DMF (227 ml) and stirred at 5° C. To this solution were added Fmoc-Lys(Boc)OH (30 g), HOBt(10.8 g), and EDC× HCl (15 g) and EtOAc (45 ml). The mixture was agitated at 20° C. to complete conversion (normally <1 h). On completion, BAEA (34.5 ml) was added and the mixture was agitated for 30 min for complete removal of the Fmoc group. On completion, the reaction mixture was washed with a mixture of NaCl (23%, 170 ml) and water (150 ml) once, and with NaHCO3 (4.8%, 113 ml) twice. The organic layer was diluted with EtOAc (30 ml), and was ready for the next coupling. It was made sure that no aqueous phase was left behind in the reactor, and that no part of the organic layer was discarded after washings.

(c) Synthesis of Tetrapeptide H-Glu(OtBu)-Lys(Boc)-Hser(Trt)-GlyOtBu

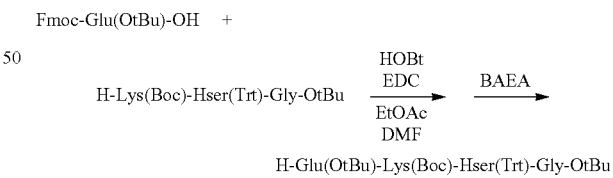

The organic solution containing the tripeptide was diluted with DMF (227 ml) and stirred at 5° C. To this solution were added Fmoc-Glu(OtBu)OH (28.5 g), HOBt(10.8 g), and EDC×HCl (15 g). The mixture was agitated at 20° C. to complete conversion (normally <2 h). On completion, BAEA (34.5 ml) was added and the mixture was agitated for 30 min for complete removal of the Fmoc group. On completion, the reaction mixture was washed with a mixture of NaCl (23%, 113 ml) and water (49 ml). The organic solution was diluted with DMF (169 ml) and EtOAc (113 ml), and then heated to 40° C. The solution was washed with a mixture of NaCl (23%, 113 ml) and water (38 ml) at 40° C. After phase separation, the organic layer was washed with a mixture of NaCl (23%, 56 ml) and water (56 ml) at 40° C. The pH of the aqeuous layer was adjusted to pH 5-5.5 (indicator sticks) with KHSO$_4$ (1 M) and the phases were separated. The organic solution was ready for next coupling. It was made sure that no aqueous phase was left behind in the reactor, and that no part of the organic layer was discarded after washings.

(d) Synthesis of Tetrapeptide FNBA-Glu(OtBu)-Lys(Boc)-HSer(Trt)-Gly-OtBu, Compound 4a

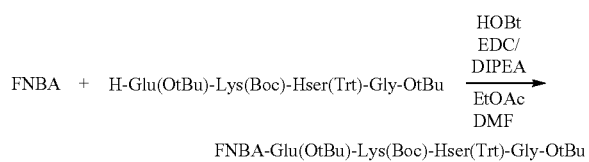

The organic solution containing the tetrapeptide was diluted with DMF (227 ml) and stirred at 5° C. To this solution were added FNBA (14.3 g), EDC×HCl (15 g) and DIPEA (13.4 ml). The mixture was agitated at 20° C. to complete conversion (normally <5 h). On completion, the reaction mixture was stirred with MeTHF (450 ml), NaCl (23%, 113 ml) and NaHCO$_3$ (4.8%, 113 ml). The layers were separated and the organic layer was heated to 40° C. and subsequently washed at this temperature with NaHCO$_3$ (4.8%, 226 ml), and finally with water (226 ml). It was made sure that no aqueous phase was left behind in the reactor, and that no part of the organic layer was discarded after washings.

The organic layer was concentrated to ca 226 ml at 40° C. under vacuum. To the residue was added MeTHF (226 ml), and then concentration to ca 226 ml was repeated. To the residue were added MeTHF (226 ml) and MTBE (450 ml), and the slurry agitated at 20° C. for 5 h. The solid product was collected on a filter and washed with MTBE (226 ml) twice and dried at 20° C. under vacuum. Dry product, compound 4a (55.6 g) was obtained, yield: 85.5% with assay correction. HPLC: 90.6%, dibenzofulvene: 9%.

(e) Partial Deprotection of the Pentapeptide (de-tritylation), Compound 3a

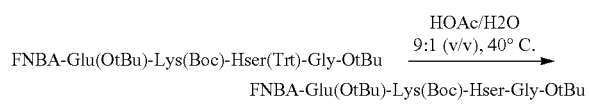

The pentapeptide (55.2 g) was added in 5-7 portions to a mixture of acetic acid (450 ml) and water (50 ml) at 40° C. After addition, the white suspension was agitated for 7-9 h to complete conversion (>98%). On completion, the reaction mixture was cooled to 20° C. and then extracted with a mixture of MTBE (552 ml), NaCl (23%, 276 ml) and water (110 ml). The organic layer was extracted twice with KHSO$_4$ (1M, 276 ml) at 20° C., three times with NaHCO$_3$ (4.8%, 276 ml) at 40° C., and once with water (276 ml). It was made sure that no aqueous phase was left behind in the reactor, and that no part of the organic layer was discarded after washings. The organic layer was cooled to 20° C. and agitated overnight to allow the product to precipitate. Heptane (552 ml) was added to the slurry, which was agitated for 1 h (more product precipitated). The solid product was collected on a filter and washed twice with heptane (2×276 ml) and twice with DIPE (2×414 ml). After drying (52° C., 4 h) in vacuo, 39.4 g of the desired partially deprotected linear peptide, compound 3a, was obtained, yield: 93% without assay correction.

(f) Cyclization

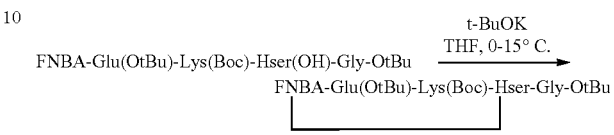

A slurry of t-BuOK (8.13 g) in THF (196 ml) was added to a cold (−8 to −1° C.) solution of the partially deprotected linear peptide (39.4 g) in THF (1560 ml). The mixture was agitated for 15-20 min (inner temperature rose to 4° C.) to obtain complete conversion. On completion, aqueous HCl (0.1 N, 189 ml) was added to the reaction mixture. THF was removed by vacuum evaporation at 40° C. The residue was diluted with water (200 ml) and agitated for ca 3 min. The solid crude product was collected on a filter, washed twice with water (2×200 ml), twice with DIPE (2×200 ml), and dried at 45° C. under vacuum for 2 h. The dried crude product (36.1 g) was suspended in EtOAc (788 ml). The suspension was agitated at 40° C. for ca 40 min. and then cooled to 0° C. and kept agitated for 2 h. The solid product, compound 2a, was collected on a filter and washed twice with DIPE (2×200 ml) on the filter. After drying, 34.6 g of the purified cyclic peptide was obtained, yield: 78.6% with assay correction, HPLC 96.8%.

(g) Final Deprotection

The purified cyclic peptide (33.3 g) obtained from the cyclization step was suspended in a mixture of MeCN (330 ml) and concentrated HCl (37%, 54 ml). The suspension was agitated at 15° C. for 1 h. The suspension turned to a solution and then to a slurry again. On completion, MeCN (330 ml) was added and the mixture was agitated for 1 h. The crude product, HCl salt of D3, was collected on a filter, washed twice with MeCN (2×330 ml), and dried at 20° C. under vacuum. Yield: 24.5 g.

(h) Crystallization

Basification-Acidification Method:

The crude product (24.5 g) was suspended in water (245 ml) and heated to 50° C. To this suspension (may appear as a gel) was added NaOH (2 M, 47.6 ml). The mixture was stirred at 50° C. for 1 h until a solution was obtained (may be cloudy). This solution was filtered hot to remove any insoluble materials. The vessel was rinsed with water (74 ml), the rinsing liquid was passed through the filter, and filtrates were combined. The combined filtrates were transferred to another vessel, and heated to 50° C. with efficient agitation. To this warm solution was added HCl (4 M, 47.6 ml). A gel was formed initially. The agitation was continued at 50° C. for 40 min, at 40° C. for 50 min, at 30° C. for ca. 14 h, and at 1° C. for 8 h to obtain a white slurry. The purified final product (white needles) was collected on a filter, washed with HCl (1 M, 50 ml) and dried at 20° C. under vacuum. Yield: 21 g, assay: 85.66%. HPLC: 98.9%. Overall yield: 53.6% with assay correction starting from Fmoc-Hser(Trt)OH.

The final product tended to from a gel at pH 2-8, but at pH>9 it formed a stable solution appropriate for clear filtration. After acidification of the clear solution with 37%

Figure 3:
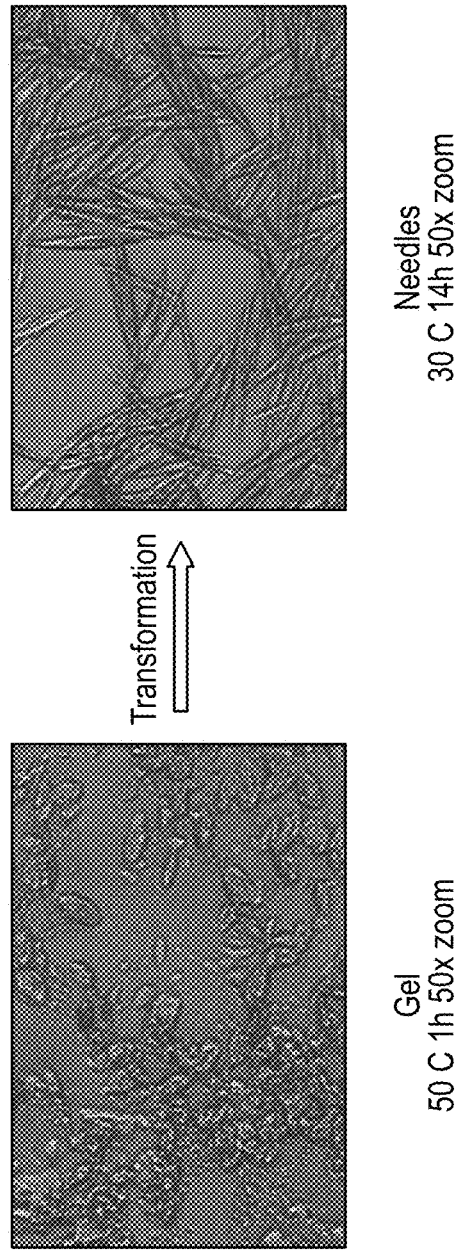
FIG. 3 shows microscope images illustrating the crystal transformation of the crystal of D3 from irregular shape present in a gel to needle-like crystals present in an acidic solution.

HCl to pH≤<0, the final product HCl salt formed a gel first and then the gel was transformed to fine needles (see, FIG. 3) of high purity.

Example 2

Optimization of the Crystallization Process

A series of experiments were performed to avoid formation of impurities during the crystallization and to obtain a robust process at larger scale. The temperature and the strength of HCl were varied and summarized in Table 1 below. A sample was removed from each experiment at a certain time: 2 h, 4 h, 8 h and 22 h. The content of the final product and the three major impurities in the samples were monitored with HPLC (FIG. 4-7).

TABLE 1

|  | 40° C. | 50° C. | 60° C. |
|---|---|---|---|
| 5 equiv. HCl | A | B | C |
| 7 equiv. HCl | D | E | F |

Figure 4:
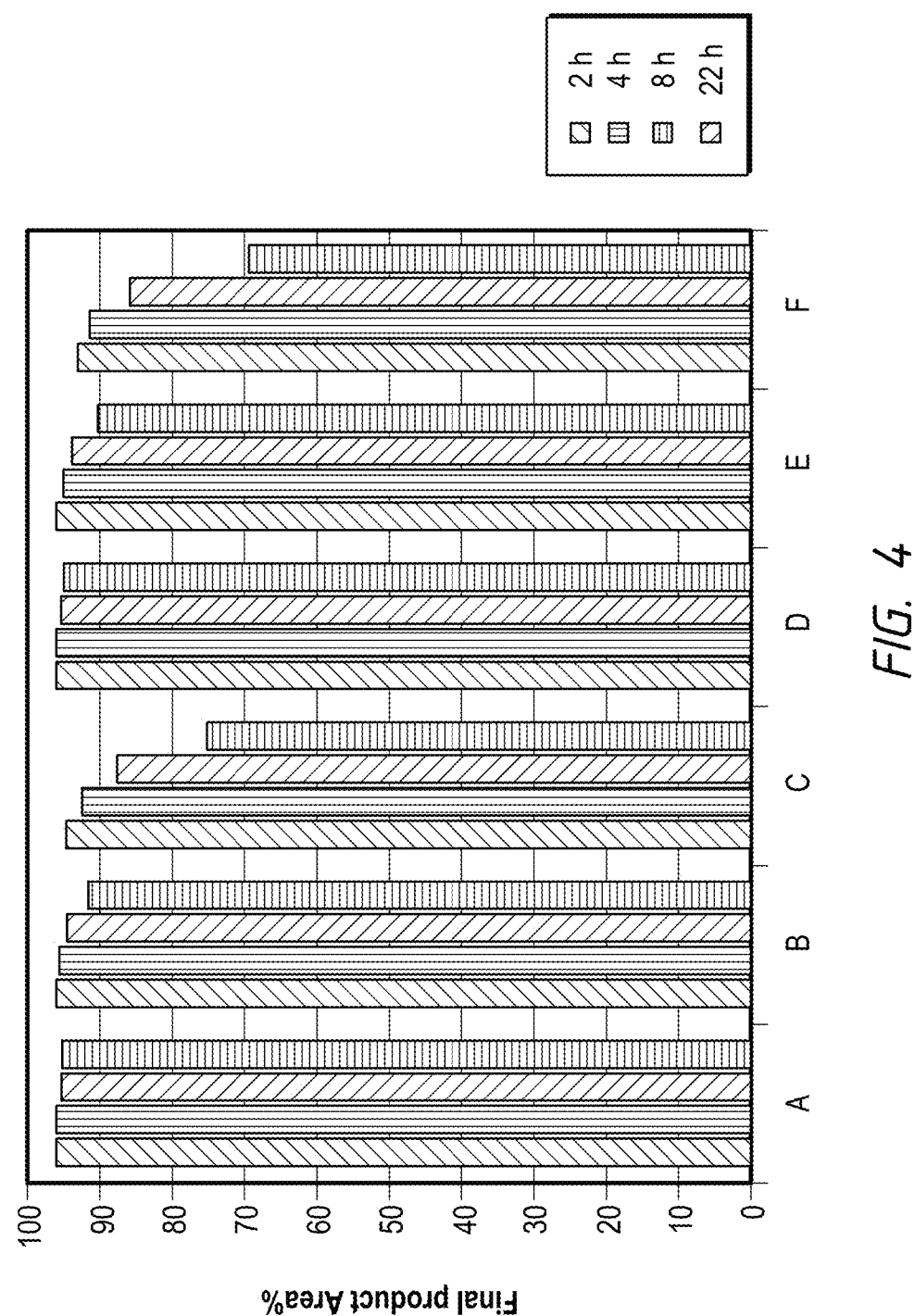
FIG. 4 is a bar chart showing the content of the salt of β-turn peptidomimetic cyclic compound of formula (I) prepared according to embodiments of the disclosure after treatment with various concentration of HCl at different time during crystallization.

FIG. 4 is a bar chart showing the HPLC percent area of the final product at different conditions (i.e., at various temperature and concentration of HCl (labeled as A, B, C, D, E and F)) at 2 hours, 4 hours, 8 hours and 22 hours during crystallization. The starting purity was 96.2%.

Figure 5:
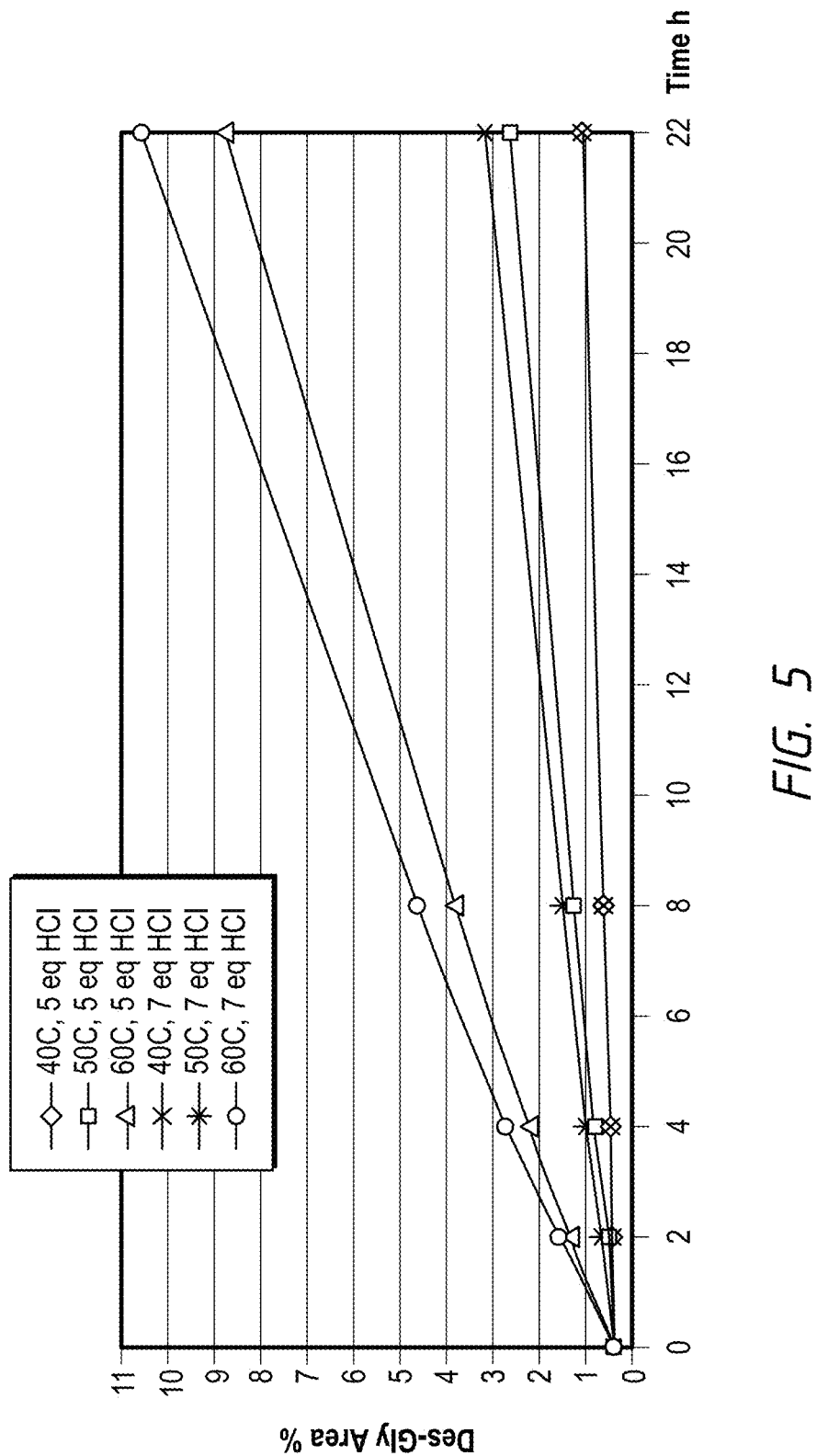
FIG. 5 is a graph showing the content of an impurity produced during the crystallization step over time according to an embodiment of the disclosure.

FIG. 5 is a graph showing the formation of impurity Des-Gly during crystallization over time a period of 22 hours. The following conclusions can be made: (a) at 40° C., the final product is stable in the presence of 5 and 7 equiv. of HCl for 22 hours; (b) at 50° C., the final product is stable in the presence of 5 and 7 equiv. HCl for 4 hours; (c) at 60° C., the final product starts to degrade after 2 h.

Figure 6:
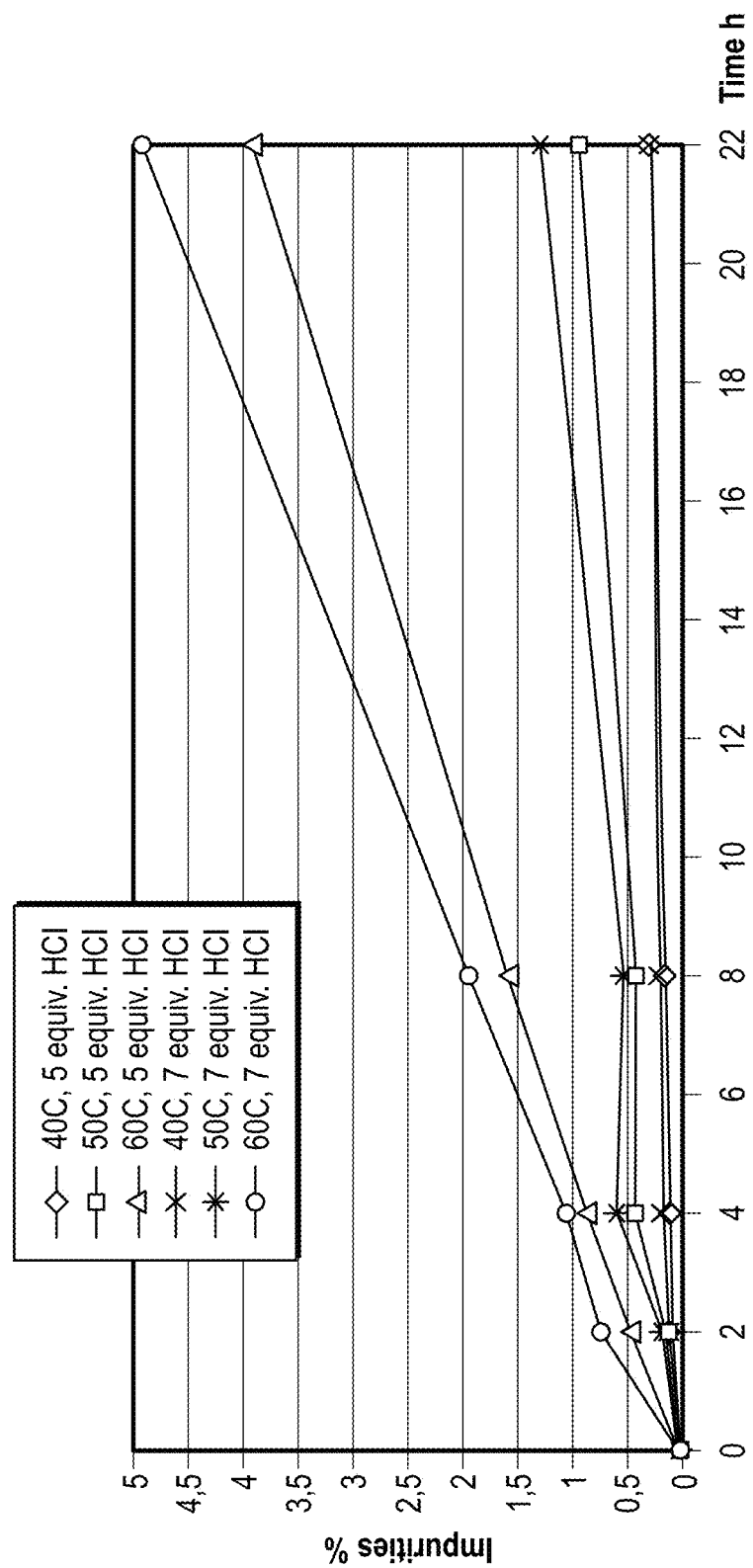
FIG. 6 is a graph showing the content of another impurity produced during the crystallization step over time according to an embodiment of the disclosure.

FIG. 6 is a graph showing the formation of an unknown impurity during crystallization over time a period of 12 hours. The impurity was eluted at 0.93 relative retention time (RRT0.93) measured by the HPLC. The following conclusions can be made: (a) at 40° C., the formation of RT0.93 is very slow regardless if it is added 5 equiv. or 7 equiv. HCl; (b) at 50° C., the formation of RT0.93 is slightly higher than that at 40° C. within 8 hours. It is accelerated after 8 h, and more RT0.93 is generated using 7 equiv. HCl compared to 5 equiv. HCl; (c) at 60° C., the formation of RT0.93 is increased rapidly.

Figure 7:
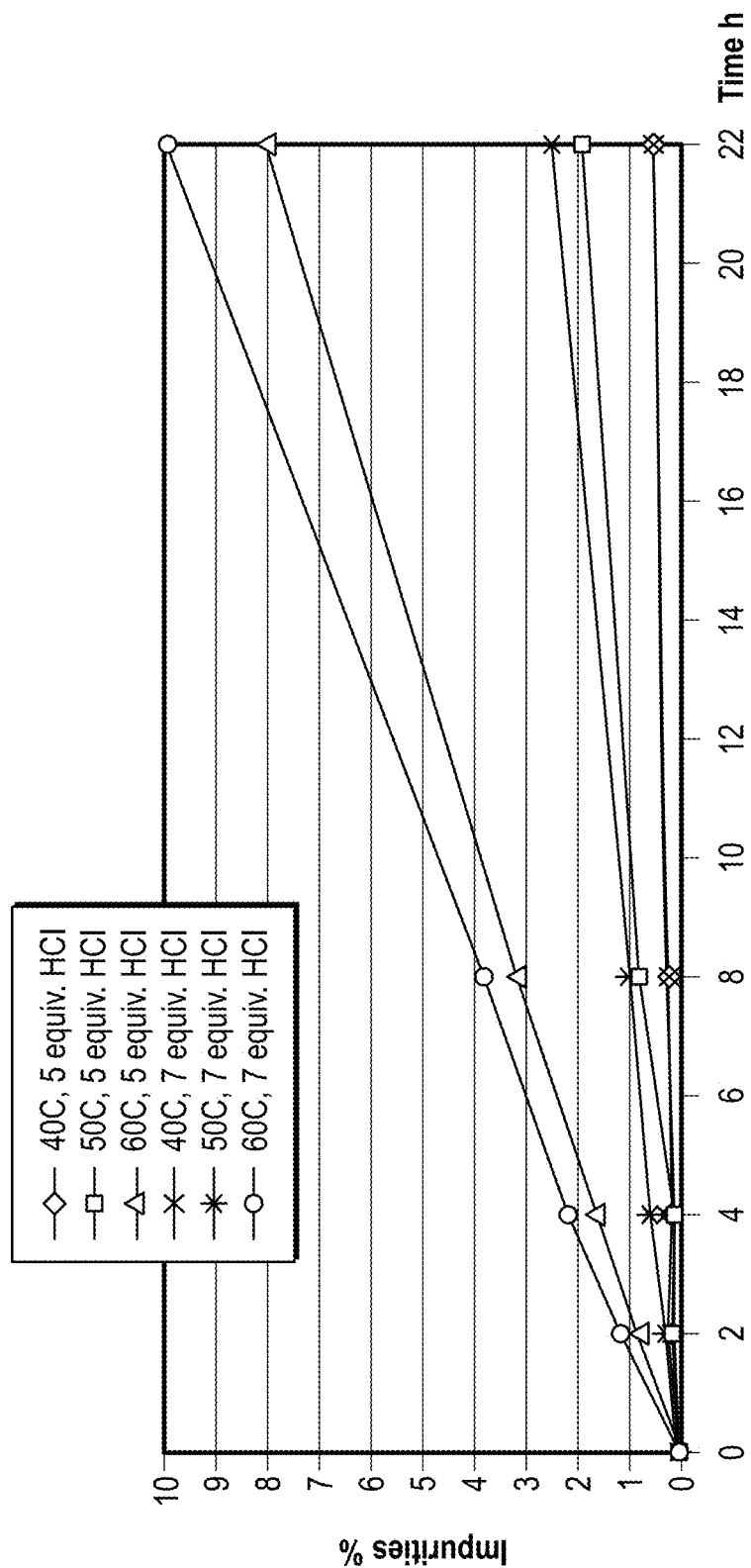
FIG. 7 is a graph showing the content of yet another impurity produced during the crystallization step over time according to an embodiment of the disclosure.

FIG. 7 is a graph showing the formation of an unknown impurity during crystallization over time a period of 12 hours. The impurity was eluted at 1.11 relative retention time (RRT1.11) measured by the HPLC. The following conclusions can be made: (a) at 40° C., the formation of RRT1.11 is very slow regardless if 5 equiv. or 7 equiv. HCl are added; (b) at 50° C., the formation of RRT1.11 is slightly higher than at 40° C. within 4 hours. It is accelerated after 4 h, and more of the unknown impurity is generated using 7 equiv. HCl than using 5 equiv. HCl; (c) at 60° C., the formation of RRT1.11 is increased rapidly.

Example 3

Temperature Cycling During Crystallization

Figure 8:
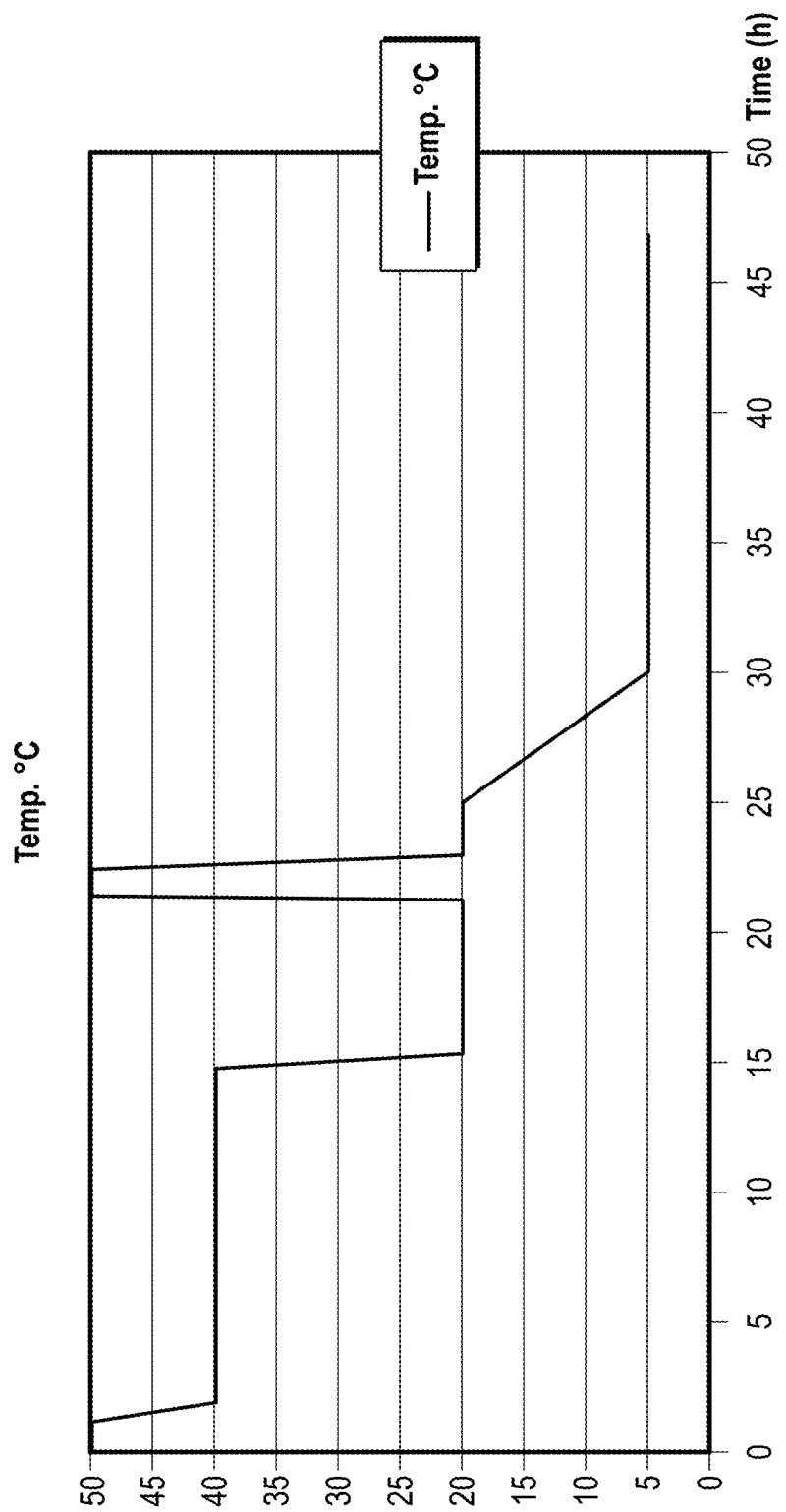
FIG. 8 is a diagram of a temperature cycling profile for the crystallization step according to an embodiment of the disclosure.
Figure 9:
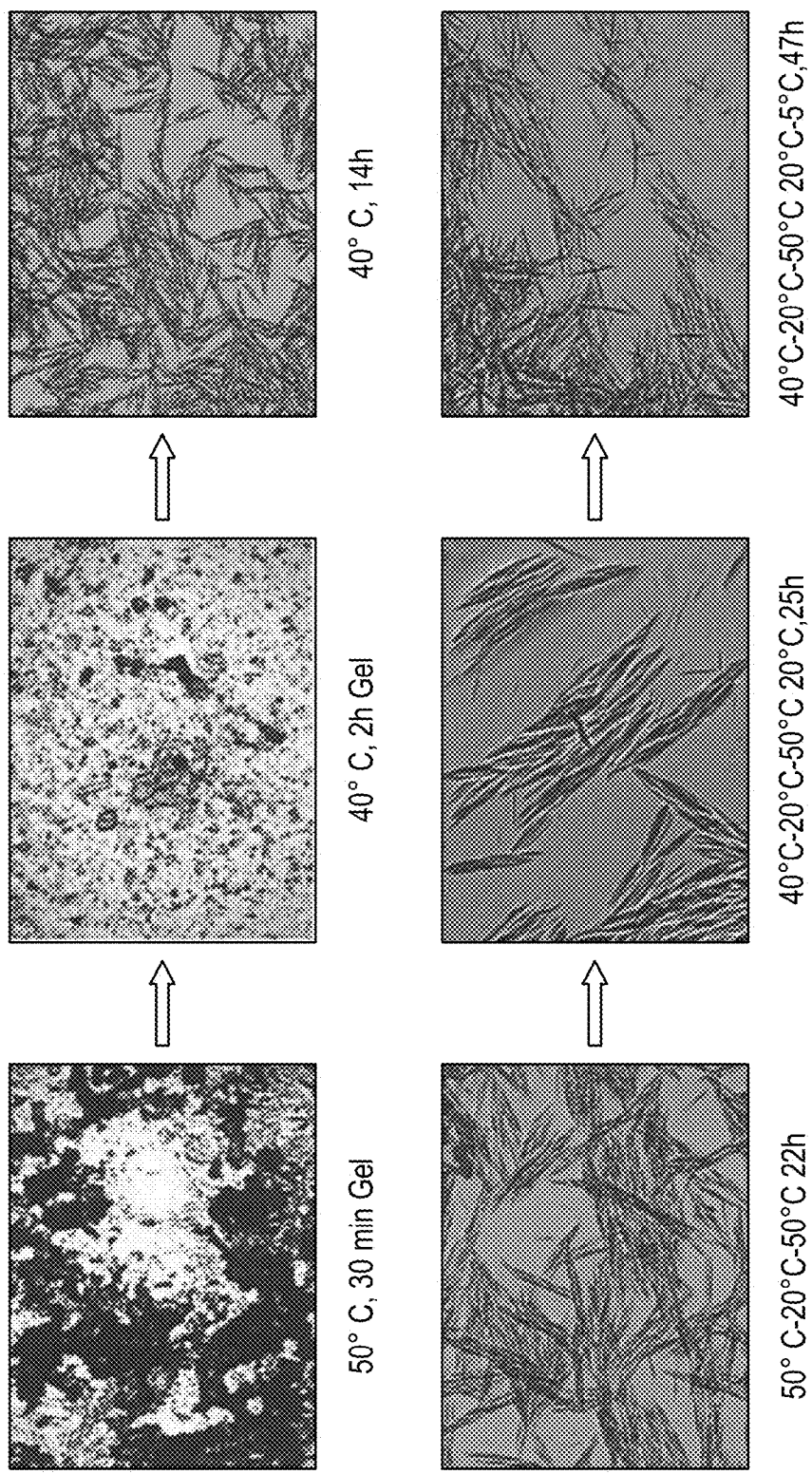
FIG. 9 shows microscope images illustrating the appearance of the crystal of D3 HCl salt from irregular shape present in a gel to needle-like crystals present in an acidic solution.

In order to understand the crystallization process, the temperature was cycled during the crystallization by lowering it from 50° C. to 20° C., and then raising it to 50° C. and lowering to 20° C. again. The temperature cycling diagram is shown in FIG. 8. Samples were removed from the slurry at intervals and analyzed by microscopy. FIG. 9 shows the crystal transformation of the final product under microscope analysis.

Figure 10:
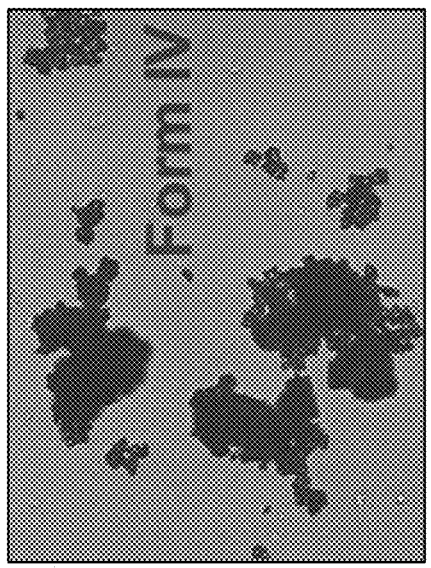
FIG. 10 shows microscope images illustrating the crystal transformation of the crystal of D3 HCl salt from crystalline form V to form IV upon drying.
Figure 10:
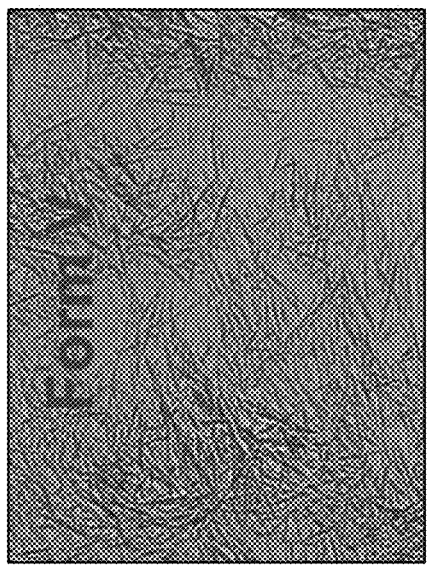

A gel was transformed to a crystalline (needles) slurry after 14 hours at 40° C. These needles were not damaged during the temperature cycling for totally 47 hours, including long cooling at 5° C. This means that this crystalline form was stable under these conditions and the transformation required a long time. Throughout development of the crystallization method several experiments indicated that the purity of the crude final product influences the transformation rate from gel to crystalline material. After crystallization, the purity of the crystalline product was above 97% (e.g., 97.2%-99.1%) measured by HPLC. The crystalline product was easier to filter than the gel, although the filtration time was relatively long. After drying, the needles were transformed to an irregular solid, with some crystallinity. FIG. 10 shows the crystal transformation on the filter under microscope analysis.

Example 4

Studies of Transformation of Crystal Forms

Figure 11:
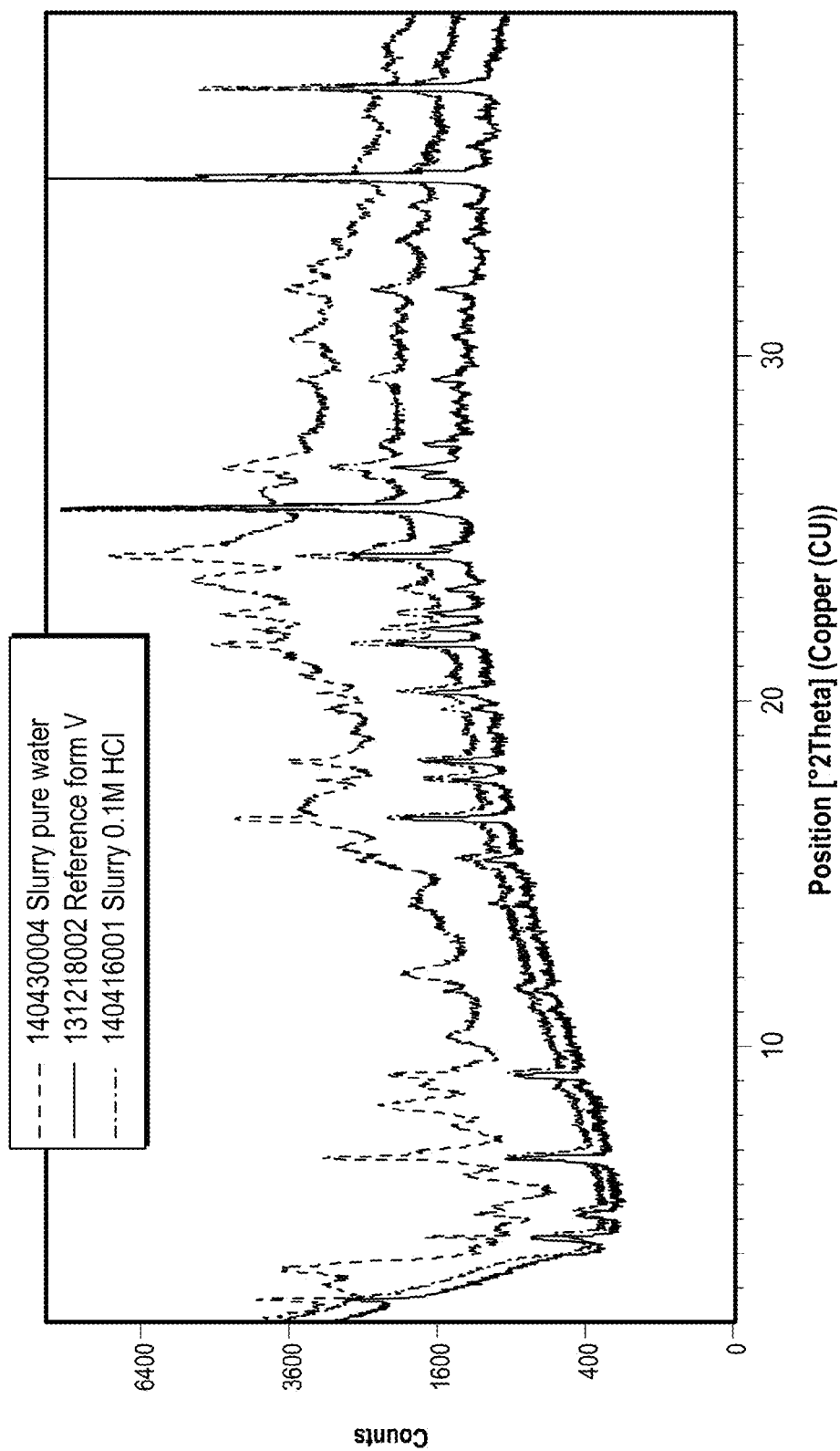
FIG. 11 is a result of the XRPD (X-ray powder diffraction) analysis of a crude D3 HCl salt slurry in 0.1M HCl solution.

A crude batch of D3 sample was slurried in 0.1M HCl solution, 0.001M HCl solution to study possible transformations. Approximately 60 mg of crude D3 sample was slurried in 0.6 ml solution. The slurry was left with magnetic stirring at room temperature. In the 0.1M HCl slurry, needles were observed after 1-2 days. The slurry was analyzed by XRPD on a porous plate, see FIG. 11. The crystal form corresponds to form V, i.e., a fast transformation from form IV to form V occurs. In pure water, the transformation was much slower and an analysis was made after 2 weeks. The slurry includes mainly form V but there are some extra peaks which may indicate the presence of other forms. It should be noticed that the crude material may have contained excess amounts of HCl which influences the pH. The pH in the pure water slurry was approximately 3.

Figure 12:
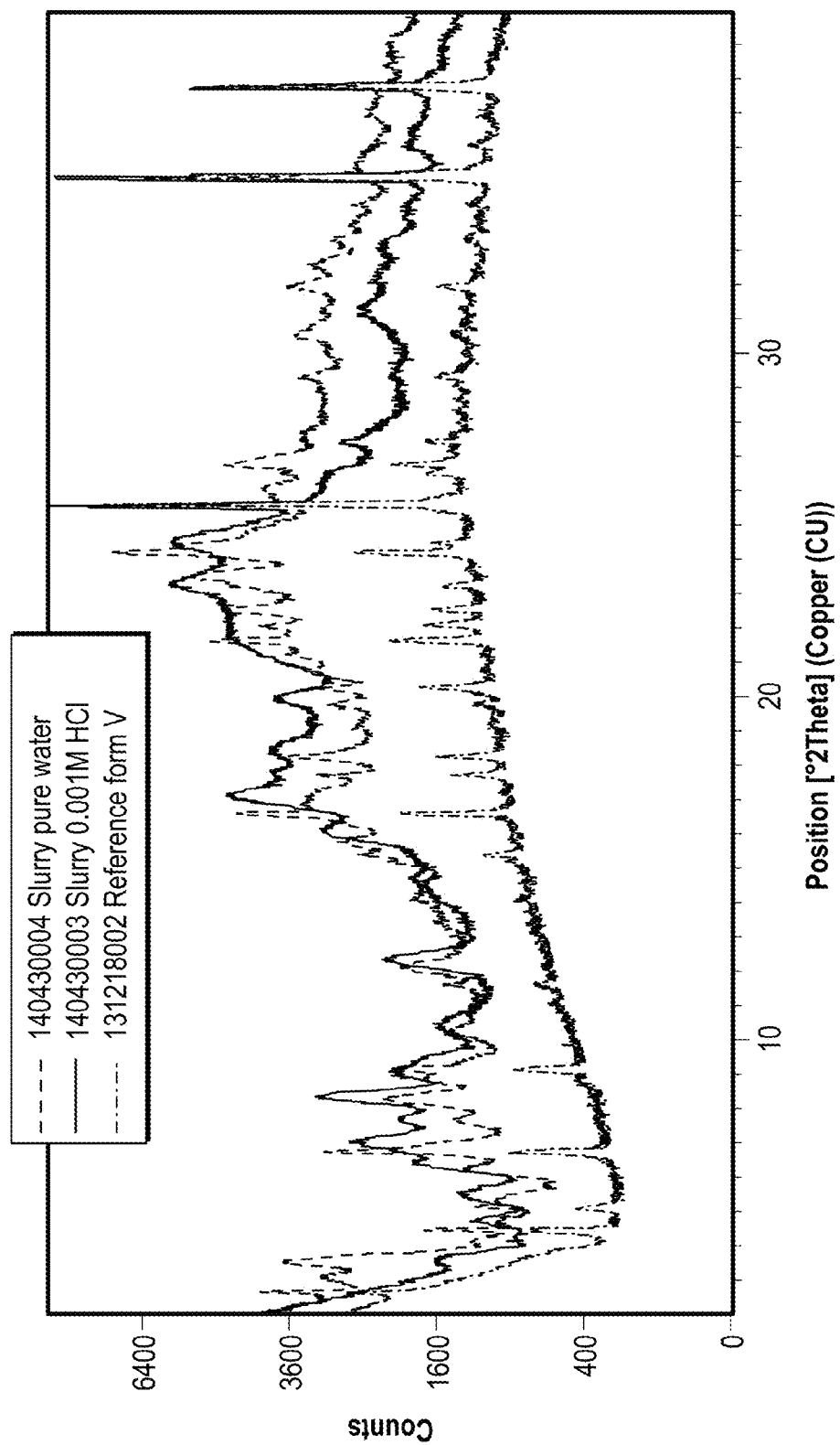
FIG. 12 is a result of the XRPD analysis of a crude D3 HCl salt slurry 0.001M HCl solution.

In 0.001M HCl solution, the transformation was also slow and the analysis was made after 2 weeks. The XRFD, see FIG. 12, shows that crystalline material had formed. There are a lot of similarities with the pure water (i.e., 100% water) slurry, i.e., it seems to be a mixture of form V and some other form.

The 0.1M HCl slurry was analysed a second time after 3 weeks. See FIG. 13a. It is still corresponding to form V, i.e., the slurry seems very stable with respect to polymorphic form.

Example 5

Characterization of the Amorphous Form of D3

Figure 14:
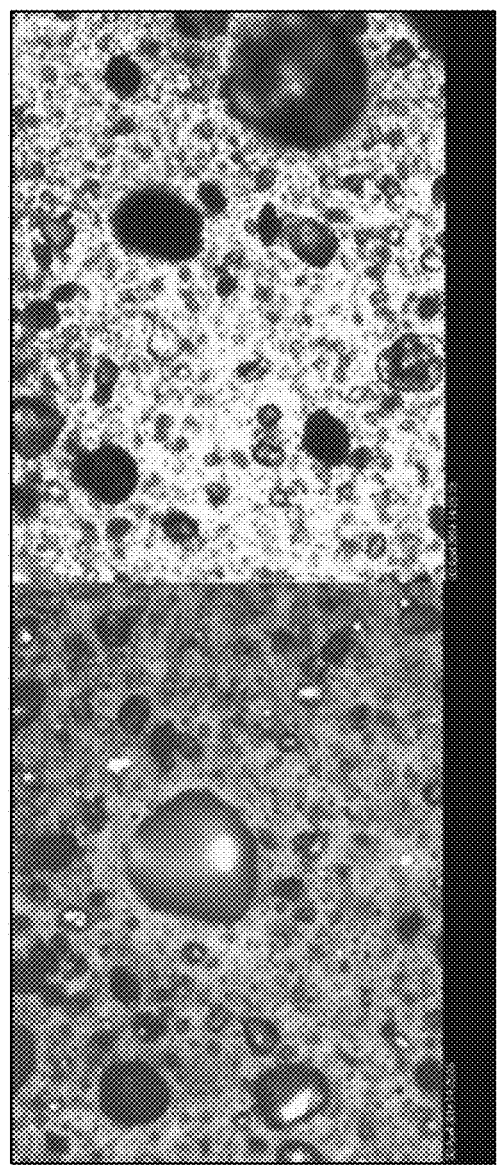
FIG. 14 shows microscope images illustrating the form IV of D3 HCl salt according to an embodiment of the disclosure.

FIG. 14 shows microscope pictures of a dry sample of an amorphous HCl salt of D3, which was crystallized but lost its crystallinity upon drying which was obtained prior to crystallization.

Figure 15:
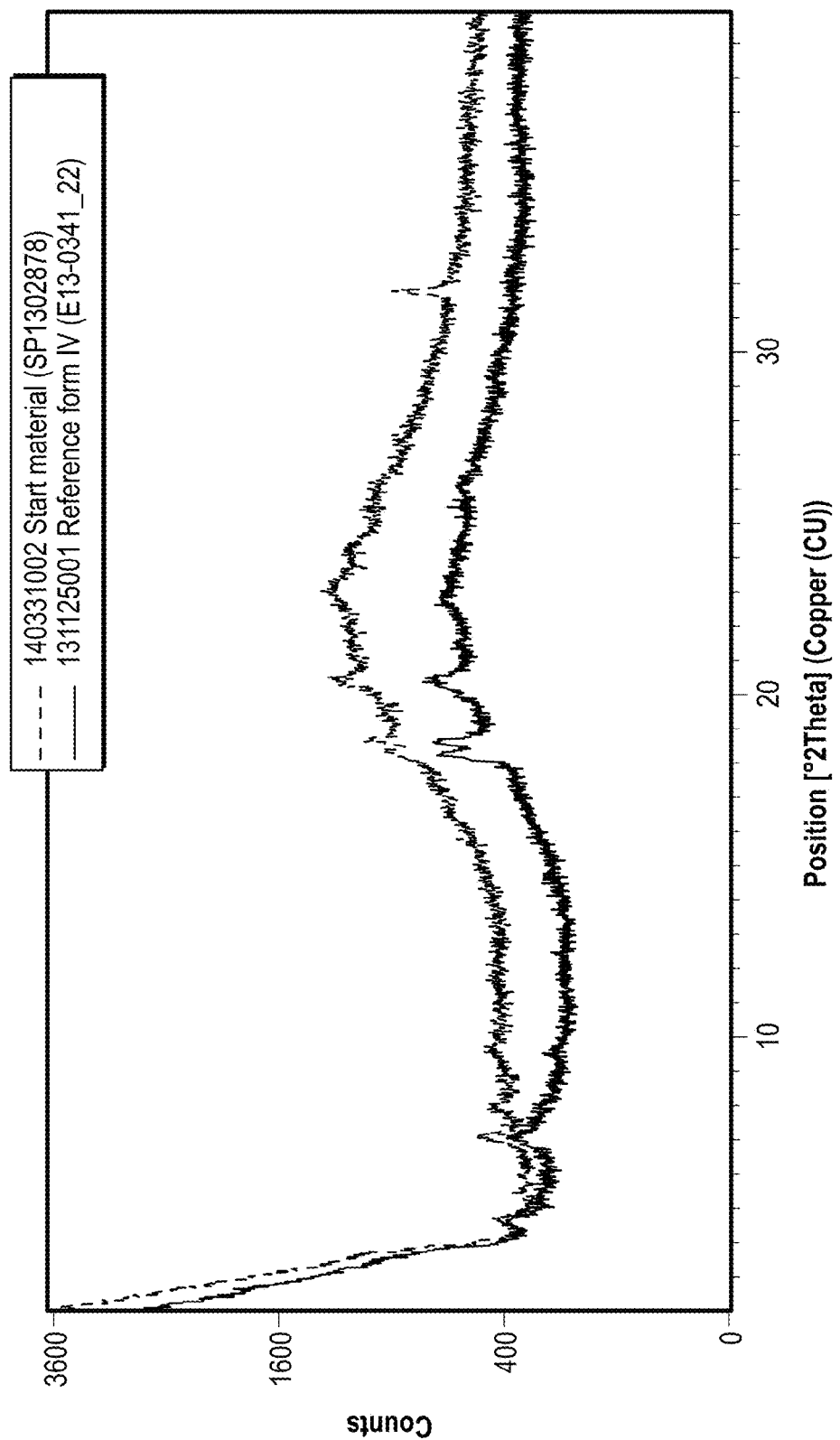
FIG. 15 is a result of the XRPD analysis of an amorphous HCl salt of D3 sample.

The amorphous HCl salt of D3 sample was analyzed by XRPD, see FIG. 15. It can be concluded that the material is form IV although it is mainly amorphous. The peak at 2Theta=32° corresponds to sodium chloride in the material.

Figure 16:
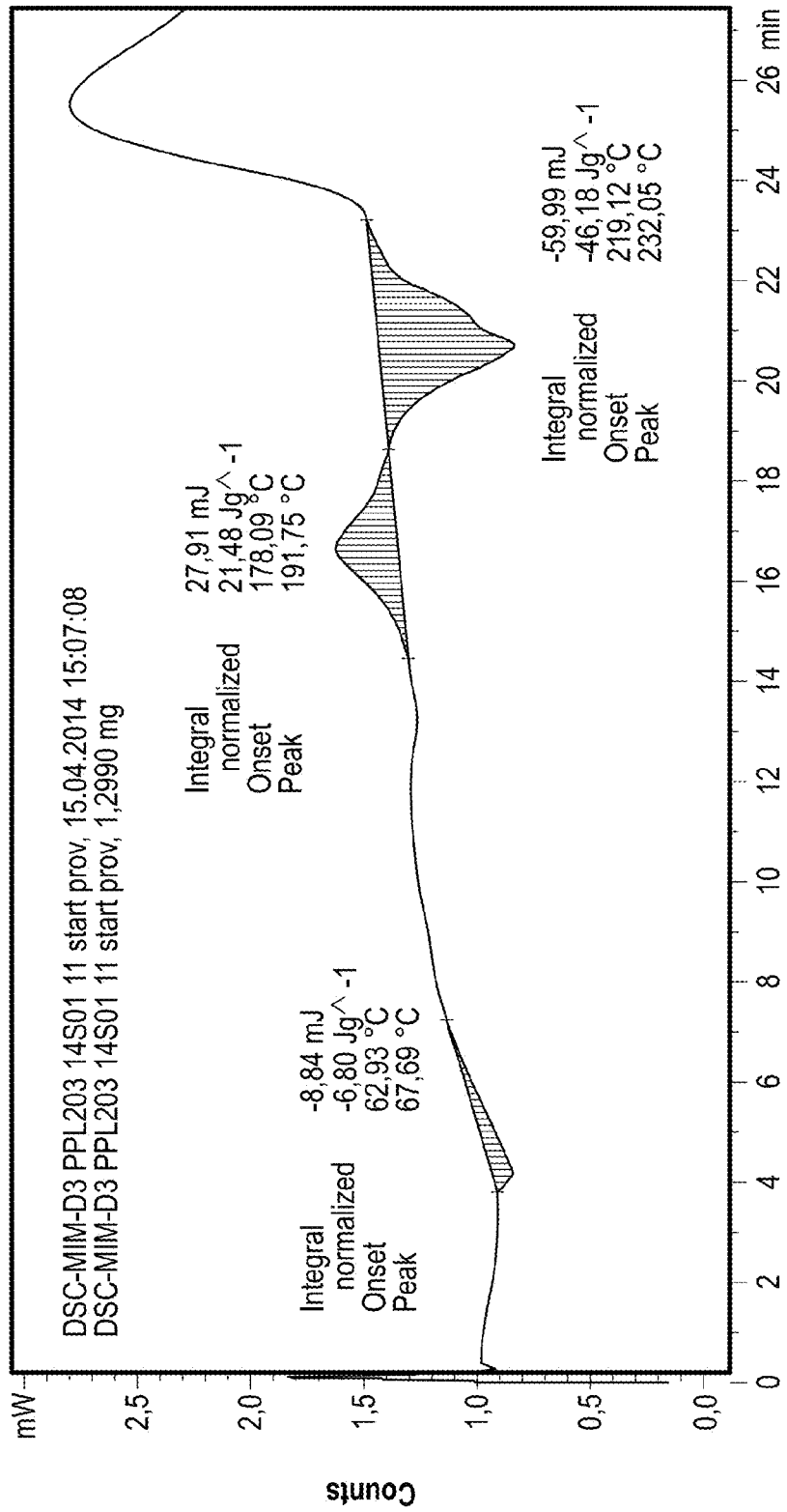
FIG. 16 is a differential scanning calorimetry (DSC) of an amorphous HCl salt of D3.

The DSC of the amorphous HCl salt of D3 is shown in FIG. 16. There is a small endotherm around 60° C., a week exothermic event around 180-190° C. followed by an endotherm around 220° C. Since form IV is mainly amorphous it is expected that the thermal events are smaller and not well defined.

Figure 17:
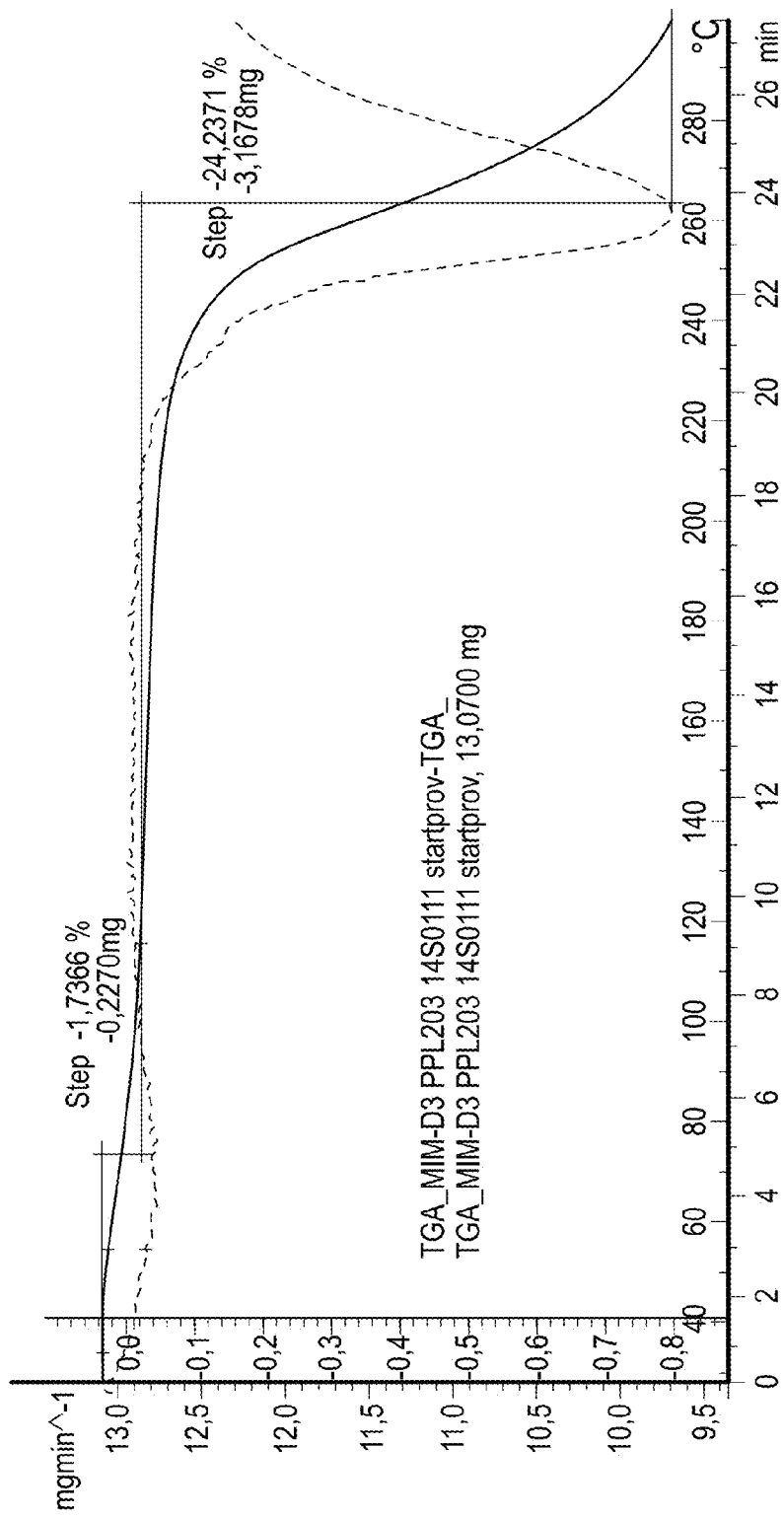
FIG. 17 is a thermogravimetric analysis (TGA) of the amorphous HCl salt of D3.

The thermogravimetric analysis (TGA) of the amorphous HCl salt of D3 is shown in FIG. 17, which shows a weight loss of approximately 1.7% up to 100-110° C.

Figure 18:
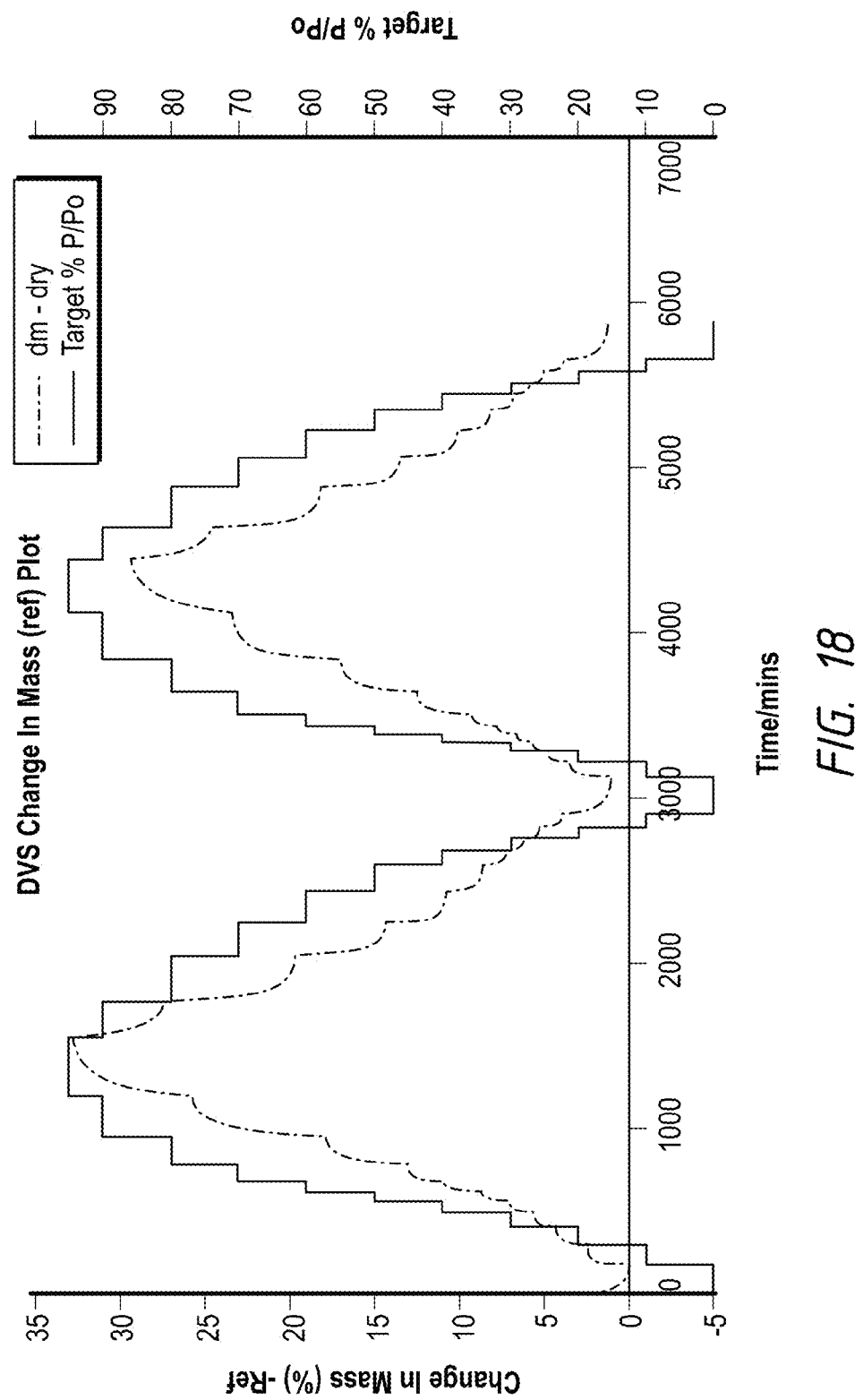
FIG. 18 is a dynamic vapor sorption (DVS) of the amorphous HCl salt of D3, showing mass change as a percentage as a function of time and target P/Po (i.e., set point relative humidity) as a function of time.
Figure 19:
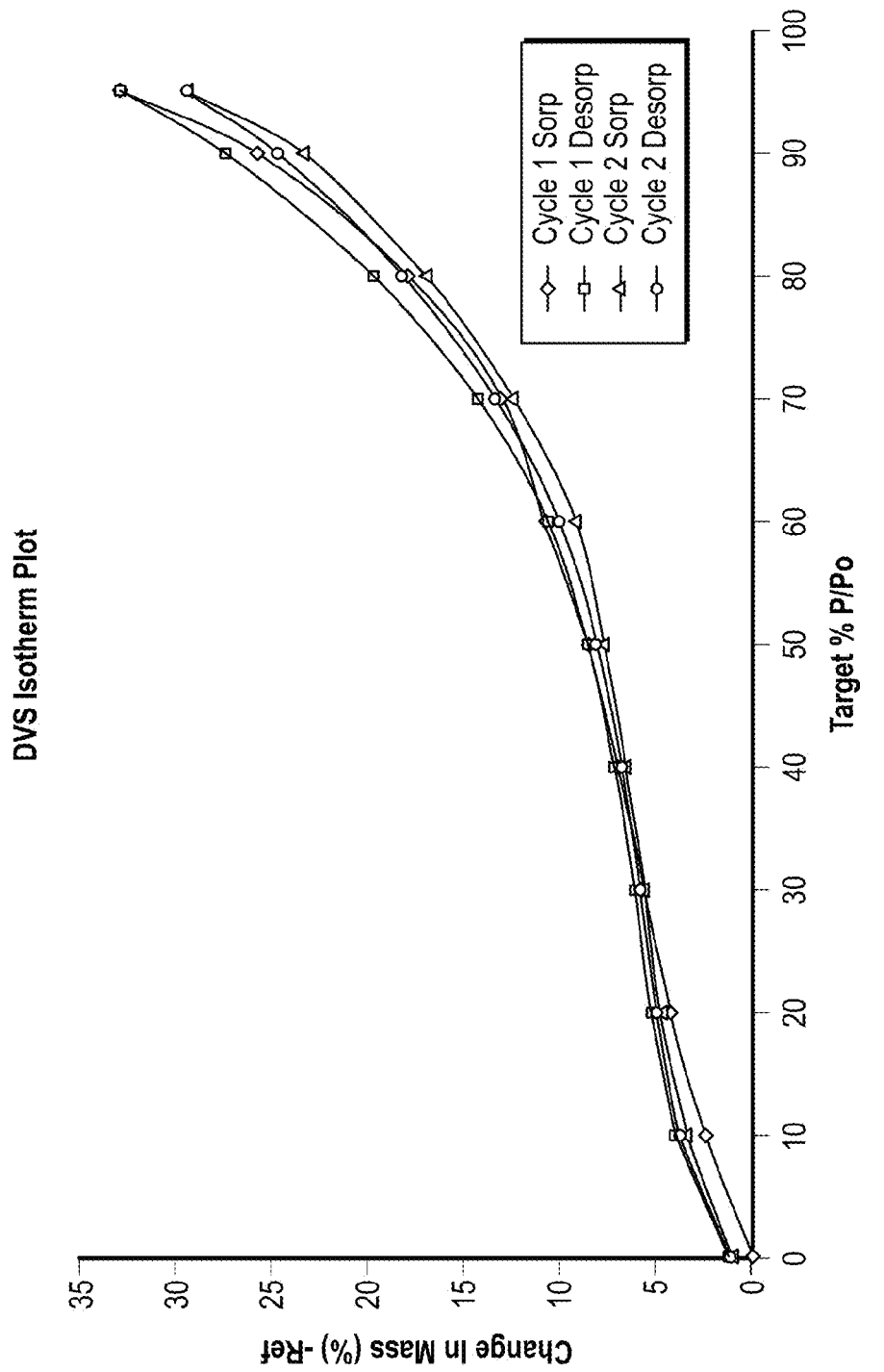
FIG. 19 is a dynamic vapor sorption (DVS) isotherm plots for the amorphous HCl salt of D3 showing change is mass versus target P/Po (i.e., set point relative humidity)

The amorphous HCl salt of D3 sample was analyzed by dynamic vapor sorption (DVS), see FIG. 18. There is a continuous uptake of water up to 95% relative humidity corresponding to a weight increase of 32%. At 20% RH (relative humidity), the change in mass is 4%, at 40% RH approximately 7%. Despite the large uptake of water, the process seems completely reversible and there is almost no hysteresis effect, i.e., the uptake and loss of weight is almost identical, see FIG. 19. It is noted that both cycles are almost identical.

Figure 20:
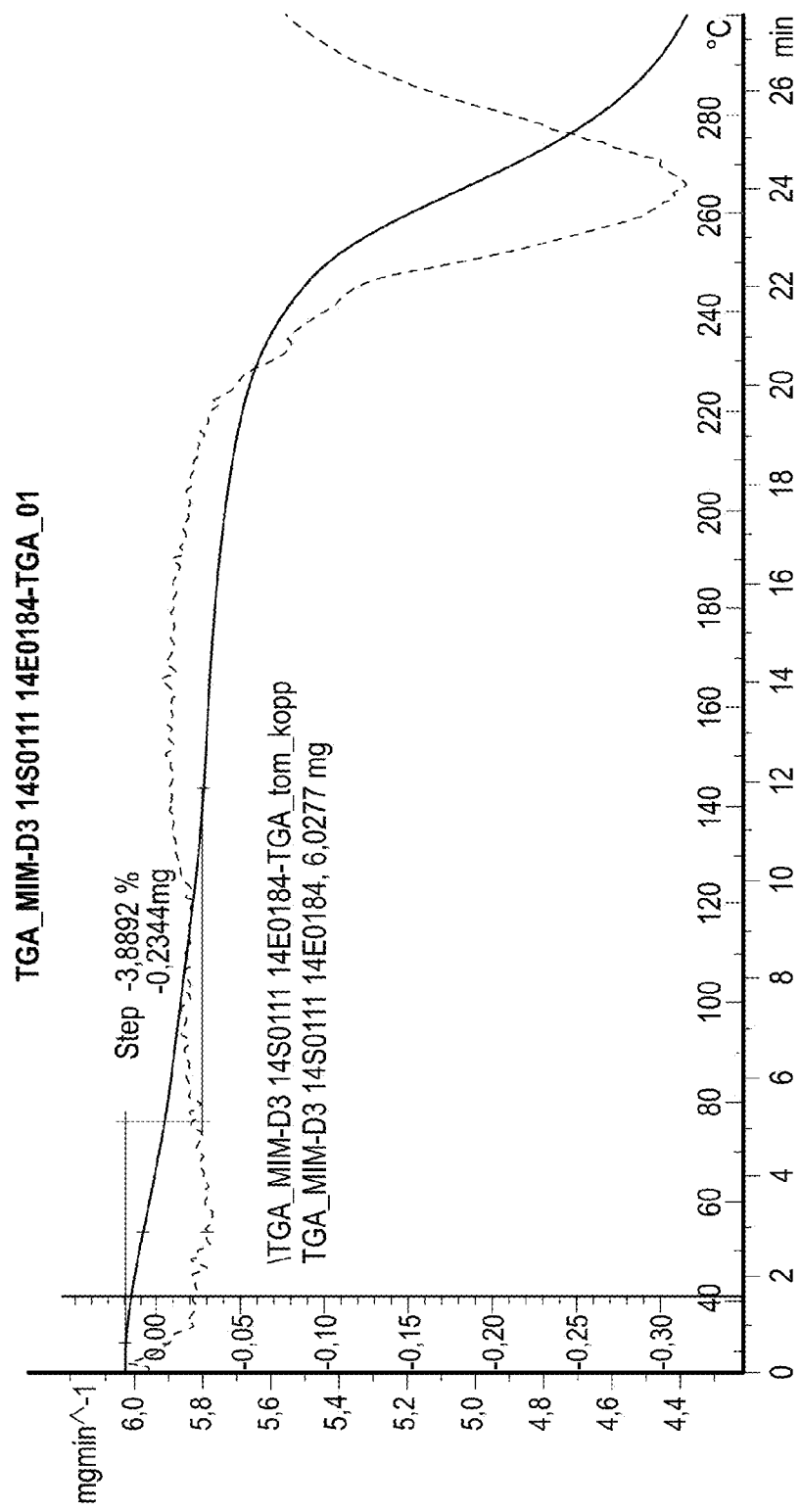
FIG. 20 is a thermogravimetric analysis (TGA) of the amorphous HCl salt of D3 material from the DVS-analysis.

The amorphous HCl salt of D3 sample after the DVS-analysis was analyzed with TGA, see FIG. 20. There is a weight loss of 3.9%, which corresponds well with the water uptake at RH=20%.

Figure 21:
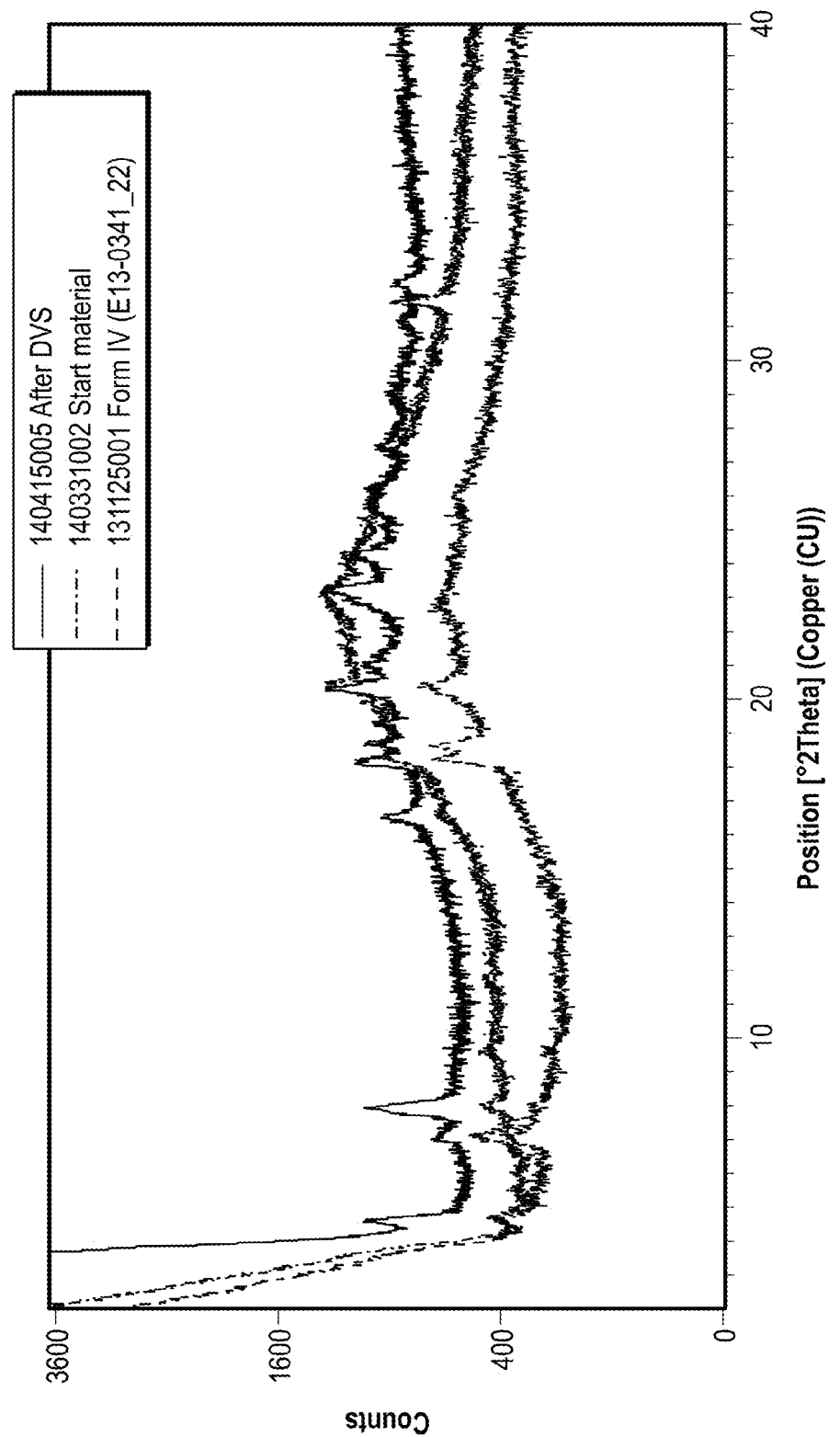
FIG. 21 is a result of the XRPD analysis of an amorphous HCl salt of D3 sample before and after DVS.

The amorphous HCl salt of D3 sample was analyzed again by XRPD, see FIG. 21, which shows that the material was still very similar to the starting material.

Figure 22:
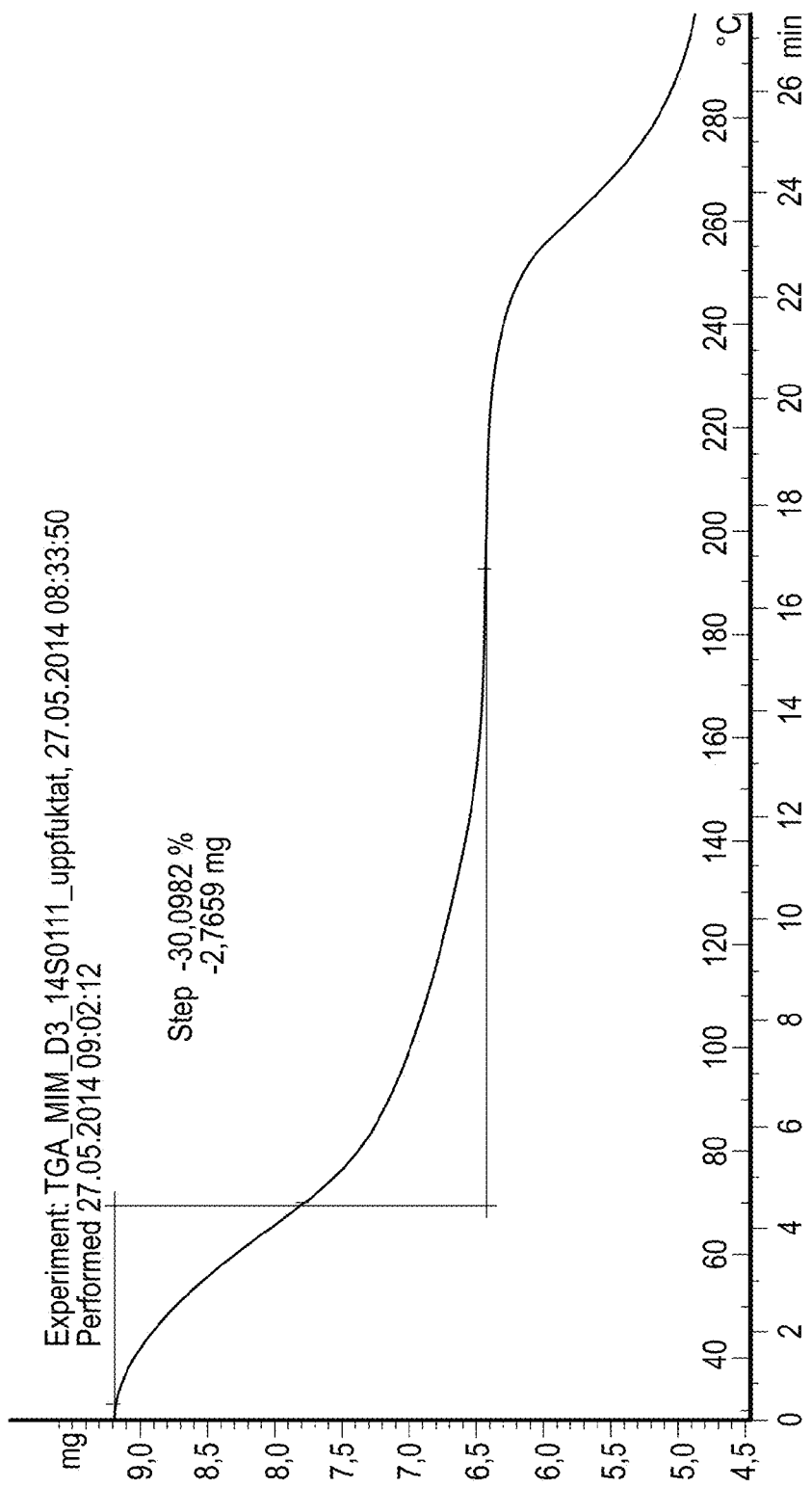
FIG. 22 is a thermogravimetric analysis (TGA) of the amorphous HCl salt of D3 after equilibrium with water vapor presented in desiccator.
Figure 23:
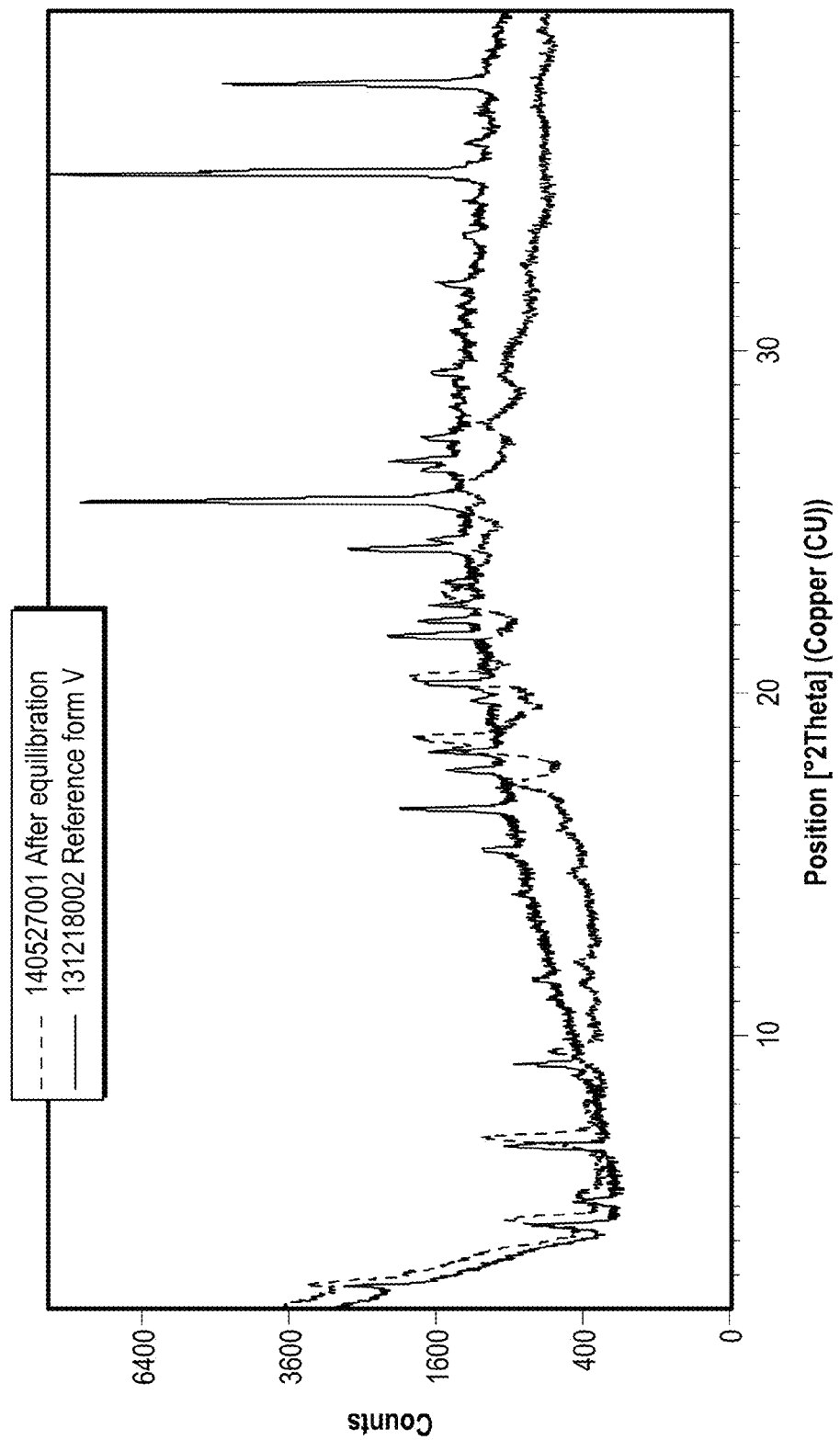
FIG. 23 is a XRPD analysis of the amorphous HCl salt of D3 after equilibration with water vapor.

In order to study the behavior at very high RH (near 100%) an amorphous HCl salt of D3 sample was added to a microscope slide and put in a desiccator saturated with water vapor. The sample was left overnight and then quickly analyzed by TGA, see FIG. 22. The TGA analysis showed a water loss of approximately 30%. It should be noticed that the sample was still in solid form, i.e., there is no deliquescence. The sample was also analyzed by XRPD, see FIG. 23. The analysis shows that the sample is more crystalline than the starting material (FIG. 21) and there is a great similarity with form V. The peaks of the reference form V are shifted towards smaller 2Theta values, i.e., towards larger d-values. This is an indication of swelling when water is added to the structure. Notice that the)(RFD-analysis was made on a ZBH and therefore the strong peaks at 2Theta=26, 35 and 38 from the porous substrate are missing.

Example 6

Methods
DSC and TGA
The DSC analysis was made on a Mettler Toledo DSC model 822. TGA analysis was made on a Mettler Toledo TGA/SDTA 851.
DVS-Analysis
A DVS analysis was made on a DVS AdVantage (Surface Measurement Systems).
XRPD
X-Ray powder diffraction patterns were collected on a PANalytical X'Pert PRO diffractometer using copper radiation equipped with PIXcel detector, automatic divergence and anti-scatter slits, soller slits and Ni-filter. The dry sample was applied to the ZBH with standard techniques for XRPD. The wet sample was analyzed by the use of porous $Al_2O_3$ plates to eliminate some of the solvent effects.
Microscope
Pictures were taken under microscope to compare with the Malvern results. The dry sample was applied on a microscope slide and some Miglyol was added. The slurry sample was analysed as it was or with a drop of Miglyol.
Equipment
Slurry experiments were performed in 4 ml vials using magnetic stirring.

While the invention has been described and pointed out in detail with reference to operative embodiments thereof, it will be understood by those skilled in the art that various changes, modifications, substitutions, and omissions can be made without departing from the spirit of the invention. It is intended therefore, that the invention embrace those equivalents within the scope of the claims that follow.

What is claimed is:

1. A crystalline form of a salt of a β-turn peptidomimetic cyclic compound having the following structure:

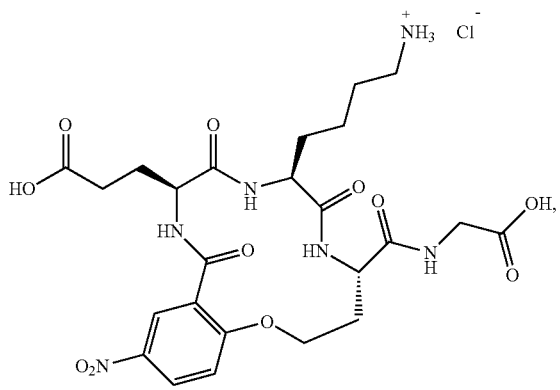 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O ; Cl]

wherein the crystalline form is obtained from a solution containing at least 60% water.

2. A crystalline form of a salt of a β-turn peptidomimetic cyclic compound having the following structure:

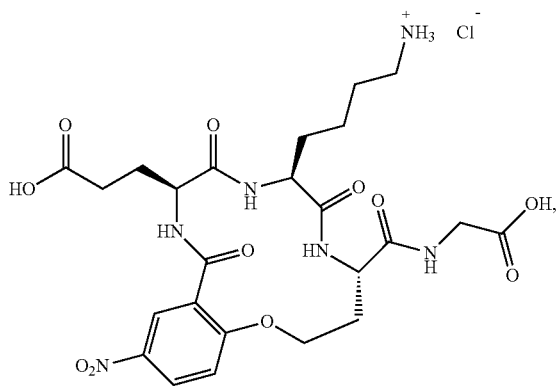 [SMILES: NCCCC[C@@H]1NC(=O)[C@H](CCC(=O)O)NC(=O)c2cc([N+](=O)[O-])ccc2OCC[C@@H](C(=O)NCC(=O)O)NC1=O ; Cl]

wherein the crystalline form is a hydrate.

3. A crystalline form of a salt of a β-turn peptidomimetic cyclic compound having the following structure:

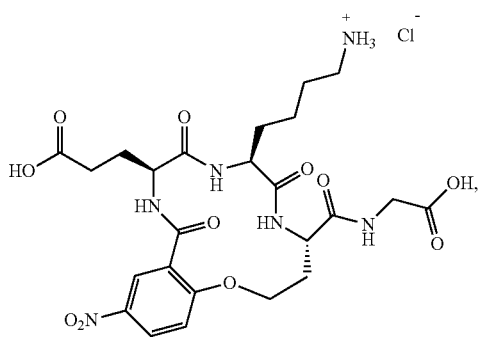 [SMILES: Cl ; NCCCC[C@@H]1NC(=O)[C@H](CCC(=O)O)NC(=O)c2cc([N+](=O)[O-])ccc2OCC[C@@H](C(=O)NCC(=O)O)NC1=O]

wherein the crystalline form is characterized by an XRPD pattern having two or more characteristic peaks at diffraction angles (° 2theta) selected from 6.7±0.2, 9.1±0.2, 4.4±0.2, 5.1±0.2, 2.6±0.2, 11.5±0.2, 15.3±0.2, 16.6±0.2, 17.7±0.2, 18.2±0.2, 20.2±0.2, 21.6±0.2, 22.1±0.2, 22.5±0.2, 23.2±0.2, 24.1±0.2.

4. A crystalline form of a salt of a β-turn peptidomimetic cyclic compound having the following structure:

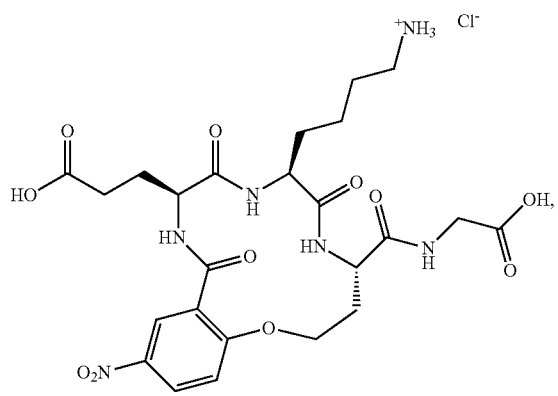 [SMILES: [Cl-] ; [NH3+]CCCC[C@@H]1NC(=O)[C@H](CCC(=O)O)NC(=O)c2cc([N+](=O)[O-])ccc2OCC[C@@H](C(=O)NCC(=O)O)NC1=O]

wherein the crystalline form is characterized by an XRPD pattern with characteristic peaks at diffraction angles (° 2theta) of 6.7±0.2, 9.1±0.2, 4.4±0.2, 5.1±0.2 and 2.6±0.2.

5. The crystalline form of claim 1, wherein the crystalline form comprises crystalline form IV having an irregular shape, crystalline form V having a needle shape, or mixtures thereof.

6. The crystalline form of claim 1, wherein the crystalline form is derived from one or more of the following intermediate compounds:

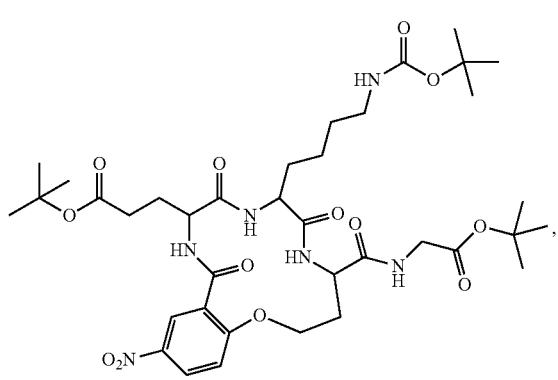

Formula (2a)

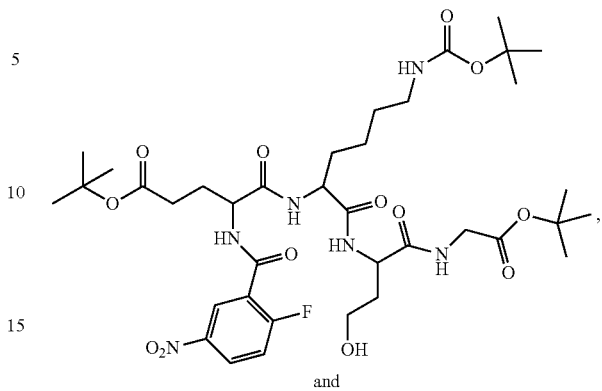

Formula (3a)

and

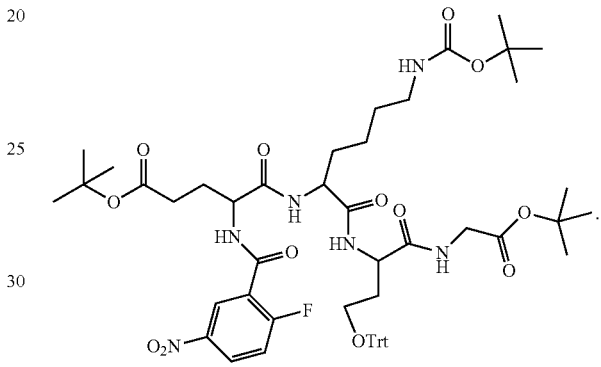

Formula (4a)

7. The crystalline form of claim 2, wherein the crystalline form comprises crystalline form IV having an irregular shape, crystalline form V having a needle shape, or mixtures thereof.

8. The crystalline form of claim 3, wherein the crystalline form comprises crystalline form IV having an irregular shape, crystalline form V having a needle shape, or mixtures thereof.

9. The crystalline form of claim 4, wherein the crystalline form comprises crystalline form IV having an irregular shape, crystalline form V having a needle shape, or mixtures thereof.

10. The crystalline form of claim 2, wherein the crystalline form is derived from one or more of the following intermediate compounds:

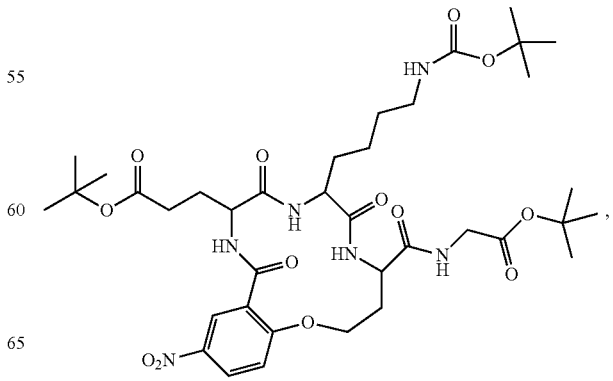

Formula (2a)

Formula (3a)
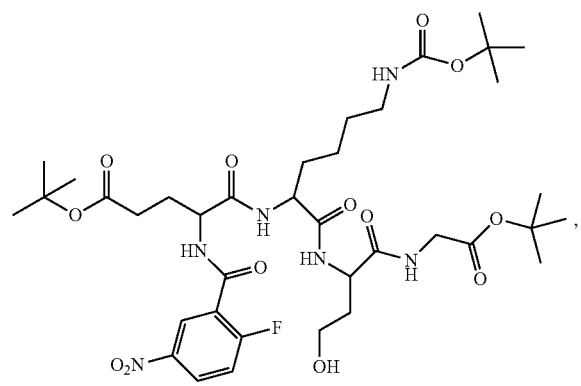
and
Formula (4a)
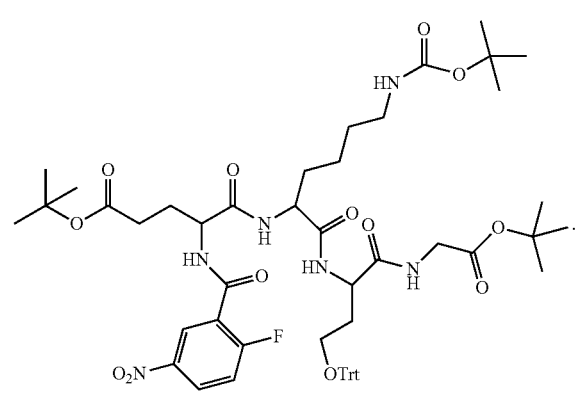
11. The crystalline form of claim 3, wherein the crystalline form is derived from one or more of the following intermediate compounds:
Formula (2a)
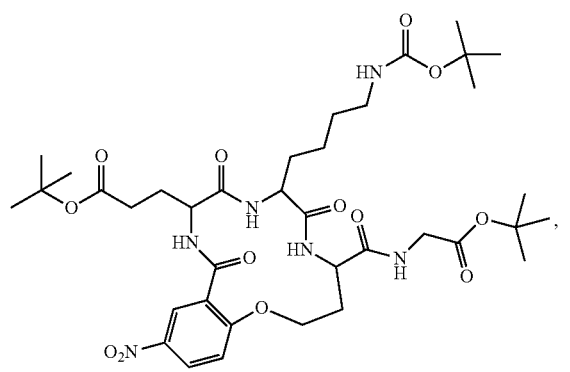
Formula (3a)
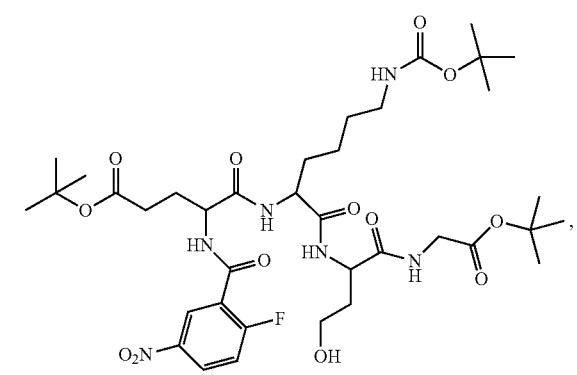
and
Formula (4a)
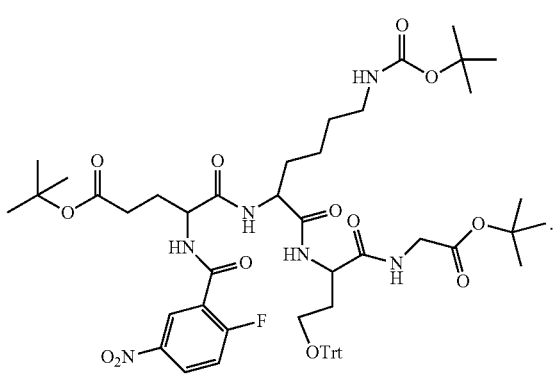
12. The crystalline form of claim 4, wherein the crystalline form is derived from one or more of the following intermediate compounds:
Formula (2a)
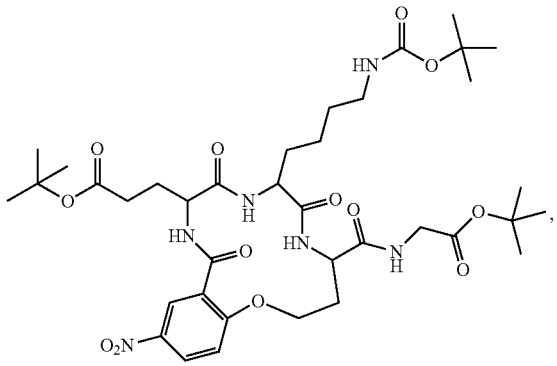

Formula (3a)
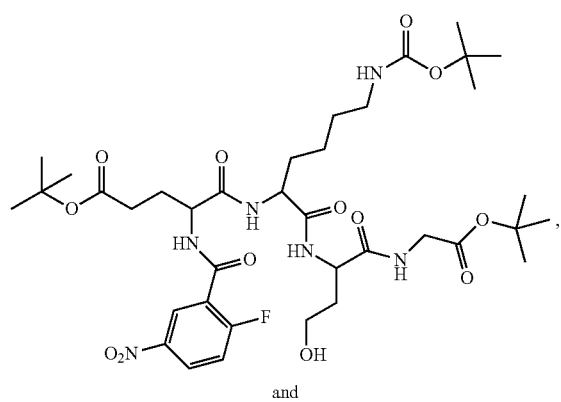
and
Formula (4a)
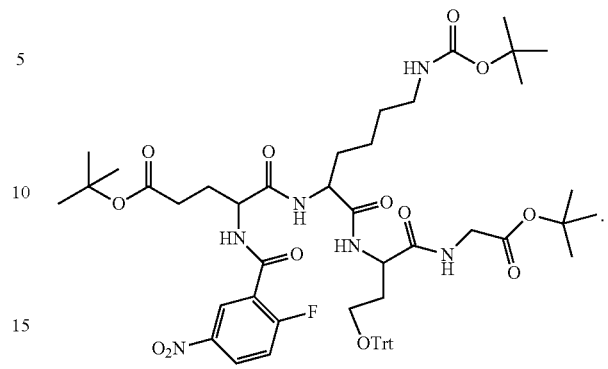
* * * * *

UNITED STATES PATENT AND TRADEMARK OFFICE
CERTIFICATE OF CORRECTION

Page 1 of 1

PATENT NO.         : 10,125,165 B2
APPLICATION NO.    : 15/205909
DATED              : November 13, 2018
INVENTOR(S)        : Sébastien Rocchi et al.

It is certified that error appears in the above-identified patent and that said Letters Patent is hereby corrected as shown below:

In the Specification

In Column 23, Line 34:
Replace "Notice that the)(RFD-analysis"
With --Notice that the XRPD analysis--

Signed and Sealed this
Sixteenth Day of April, 2019

Andrei Iancu
*Director of the United States Patent and Trademark Office*

UNITED STATES PATENT AND TRADEMARK OFFICE
CERTIFICATE OF CORRECTION

PATENT NO. : 10,125,165 B2
APPLICATION NO. : 15/205909
DATED : November 13, 2018
INVENTOR(S) : Sébastien Rocchi et al.

It is certified that error appears in the above-identified patent and that said Letters Patent is hereby corrected as shown below:

In the Specification

Column 13, Line 4:
Replace "The crystals of the salt of formula (V)"
With --The crystals of the salt of form (V)--

Column 13, Line 14:
Replace "the compound of formula (IV)."
With --the compound of form (IV).--

Signed and Sealed this
Twenty-ninth Day of December, 2020

Andrei Iancu
*Director of the United States Patent and Trademark Office*